(12) United States Patent
Androutsellis-Theotokis

(10) Patent No.: US 9,943,570 B2
(45) Date of Patent: Apr. 17, 2018

(54) MANIPULATION OF HAIRY AND ENHANCER OF SPLIT 3 (HES3) AND ITS REGULATORS/MEDIATORS AS AN ANTI-CANCER STRATEGY

(71) Applicant: TECHNISCHE UNIVERSITÄT DRESDEN, Dresden (DE)

(72) Inventor: Andreas Androutsellis-Theotokis, Dresden (DE)

(73) Assignee: Technische Universitat Dresden, Dresden (DE)

( * ) Notice: Subject to any disclaimer, the term of this patent is extended or adjusted under 35 U.S.C. 154(b) by 0 days.

(21) Appl. No.: 14/653,744

(22) PCT Filed: Dec. 20, 2013

(86) PCT No.: PCT/EP2013/077776
§ 371 (c)(1),
(2) Date: Jun. 18, 2015

(87) PCT Pub. No.: WO2014/096399
PCT Pub. Date: Jun. 26, 2014

(65) Prior Publication Data
US 2015/0320835 A1    Nov. 12, 2015

(30) Foreign Application Priority Data
Dec. 21, 2012 (EP) .................... 12199215

(51) Int. Cl.
| A61K 31/713 | (2006.01) |
| A61K 38/22 | (2006.01) |
| A61K 45/06 | (2006.01) |
| A61N 5/10 | (2006.01) |
| C12N 15/113 | (2010.01) |
| G01N 33/574 | (2006.01) |

(52) U.S. Cl.
CPC ........ *A61K 38/2278* (2013.01); *A61K 31/713* (2013.01); *A61K 45/06* (2013.01); *A61N 5/10* (2013.01); *C12N 15/113* (2013.01); *G01N 33/57488* (2013.01); *C12N 2310/11* (2013.01); *C12N 2310/12* (2013.01); *C12N 2310/14* (2013.01); *C12N 2310/141* (2013.01); *C12N 2310/16* (2013.01); *C12N 2310/531* (2013.01); *C12N 2320/30* (2013.01); *G01N 2800/7028* (2013.01)

(58) Field of Classification Search
None
See application file for complete search history.

(56) References Cited

U.S. PATENT DOCUMENTS

2009/0176724 A1*  7/2009  Shen ............... C12Q 1/6886
514/44 R

FOREIGN PATENT DOCUMENTS

| WO | WO 02/40716 A2 | 5/2002 |
| WO | WO 02/40716 A3 | 5/2002 |
| WO | WO 2014/096399 A1 | 6/2014 |

OTHER PUBLICATIONS

Androutsellis-Theotokis et al (PLoS One 5: 1-9, 2010).*
Androutsellis-Theotokis (Intl J Mol Med 28, Supplement, p. S20, 2011; Abstract 161).*
Nishizawa (Neurol Med Chir (Tokyo) 50: 713-719, 2010—abstract only).*
Gene Silencers—Santa Cruz Biotech Inc [online] Jul. 27, 2012 (retrieved on Aug. 26, 2016) (Retrieved from the Internet <URL : http://web.archive.org/web/20120727132429/http://www.scbt.com/gene_silencers_table.php?table=hes>.*
Altshuler et al "Generation of recombinant antibodies and means for increasing their affinity," *Biochemistry (Mosc)*, 2010, 75(13):1584.
Androutsellis-Theotokis et al., "Angiogenic Factors Stimulate Growth of Adult Neural Stem Cells," *PLoS One*, 2010a, 5(2):e9414.
Androutsellis-Theotokis et al., "Cholera toxin regulates a signaling pathway critical for the expansion of neural stem cell cultures from the fetal and adult rodent brains," *PLoS One*, 2010b, 5(5):e10841.
Androutsellis-Theotokis et al., "Targeting neural precursors in the adult brain rescues injured dopamine neurons," Cold Spring Harbor Laboratory Press, 2008, vol. LXXIII, pp. 1-8.
Androutsellis-Theotokis et al., "Targeting neural precursors in the adult brain rescues injured dopamine neurons," *PNAS*, 2009, 106(32):13570.
Androutsellis-Theotokis, "Notch signalling regulates stem cell numbers in vitro and in vivo," *Nature Letters*, Aug. 2006, 442(17):823-826.
Bakker et al, "C-type lectin-like molecule-1: a novel myeloid cell surface marker associated with acute myeloid leukemia," *Cancer Research*, 2004; 64(22):8443.
Bateman et al., "The Pfam protein families database," *Nucleic Acids Res.*, 2004, 32 (Database issue):D138-D141.
Black, "Brain Tumors (First of Two Parts)," *N Engl J Med.*, 1991, 324:1471-1476.
Black, "Brain Tumors (Second of Two Parts)," *N Engl J Med.*, 1991, 324:1555-1564.
Brunner et al., "Cancer Stem Cells as a Predictive Factor in Radiotherapy," *Seminars in Radiation Oncology*, 2012, 22(2):151-174.
Carbone et al., "Selective inhibition of transcription of the Ets2 gene in prostate cancer cells by a triplex-forming oligonucleotide," *Nucleic Acids Res.*, 2003, 31(3): 833-843.
Chaffer et al., "A perspective on cancer cell metastasis," *Science*, 2011, 331(6024):1559-1564.

(Continued)

*Primary Examiner* — Gregory S Emch
*Assistant Examiner* — Aditi Dutt
(74) *Attorney, Agent, or Firm* — Mueting, Raasch & Gebhardt, P.A.

(57) ABSTRACT

The present invention relates to an inhibitor of Hairy and Enhancer of Split 3 (Hes3) or for use in treating a tumor. The invention further relates to an in-vitro method for diagnosing a tumor, comprising determining the amount of Hes3 protein in a cerebrospinal fluid (CSF)-derived sample obtained from a subject, wherein an increased amount of Hes3 protein is indicative of the presence of a tumor.

13 Claims, 8 Drawing Sheets

(56) References Cited

OTHER PUBLICATIONS

Figure 1:
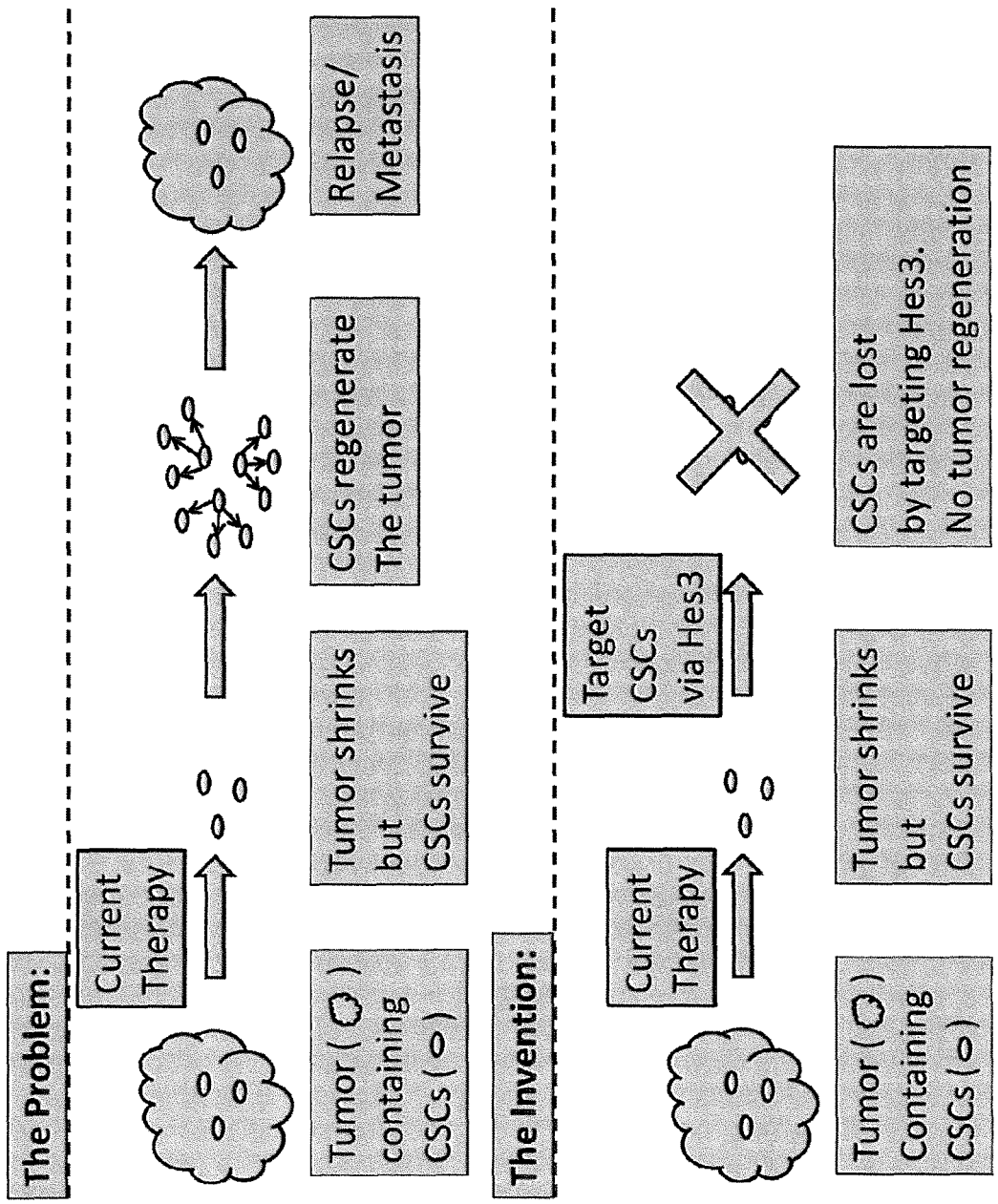

Clayton et al., Therapeutics formulated to target cancer stem cells: Is it in our future?, *Cancer Cell International*, 2011, 11(7):1-9.
De Fougerolles, "Delivery vehicles for small interfering RNA in vivo," *Hum Gene Ther.*, 2008, 19(2):125-132.
Elbashir et al., "Functional anatomy of siRNAs for mediating efficient RNAi in *Drosophila melanogaster* embryo lysate," *EMBO J*, 2001, 20(23):6877-6888.
Eng et al., "Isolation and Characterization of Exendin-4, an Exendin-3 Analogue, from Heloderma suspectum Venom," *The Journal of Biological Chemistry*, 1992, vol. 267, No. 11, pp. 7402-7405.
Fattal et al, "Nanotechnologies and controlled release systems for the delivery of antisense oligonucleotides and small interfering RNA," *Br J Pharmacol.*, 2009, 157(2): 179-194.
Gavrilov et al., "Therapeutic siRNA: principles, challenges, and strategies," *Yale J Biol Med.*, 2012, 85(2):187-200.
Hatakeyama et al., "Hes genes regulate size, shape and histogenesis of the nervous system by control of the timing of neural stem cell differentiation," 2004, *Development*, vol. 131(22), 5539-5550.
Hirata et al., "Hes1 and Hes3 regulate maintenance of the isthmic organizer and development of the mid/hindbrain," 2001, *EMBO J.*, vol. 20(16), 4454-4466.
Holliger and Hudson, "Engineered antibody fragments and the rise of single domains," 2005, *Nat Biotechnol.*, vol. 23(9), 1126-1136.
Kalinina et al., "Protemics of gliomas: initial biomarker discovery and evolution of technology," 2011, *Neuro Oncol.*, vol. 13(9), 926-942.
Kozbor and and Roder, "The production of monoclonal antibodies from human lymphocytes," 1983, *Immunology Today*, vol. 4, 72-79.
Letunic et al., "SMART 4.0: towards genomic data integration," *Nucleic Acids Res.*, 2004, vol. 32 (Database issue), D142-D144.
Li et al., "Human antibodies for immunotherapy development generated via a human B cell hybridoma technology," 2006, *PNAS*, vol. 103(10), 3557-3562.
Louis et al., "The 2007 WHO Classification of Tumours of the Central Nervous System," 2007, *Acta Neuropathol.*, vol. 114(2), 97-109.
Magee et al., "Cancer Stem Cells: Impact, Heterogeneity, and Uncertainty," 2012, *Cancer Cell*, vol. 21(3), 283-296.
Malmborg et al., "BIAcore as a tool in antibody engineering," 1995, *J Immunol Methods.*, vol. 183(1), 7-13.
Melani et al., "Inhibition of proliferation by c-myb antisense oligodeoxynucleotides in colon adenocarcinoma cell lines that express c-myb," 1991, *Cancer Research*, vol. 51(11), 2897-2901.
Mulder et al., "The InterPro Database, 2003 brings increased coverage and new features," 2003, *Nucleic Acids Res.*, vol. 31(1), 315-318.
Osborne et al., "Aptamers as therapeutic and diagnostic reagents: problems and prospects," 1997, *Curr Opin Chem Biol.*, vol. 1(1), 5-9.
Park et al., "Hes3 regulates cell No. In cultures from glioblastoma multiforme with stem cell characteristics," 2013, *Sci Rep*, 3:1095, pp. 1-9.
Paulo et al., "Mass spectrometry-based proteomics for translational research: a technical overview," *Yale J Biol Med.* Mar. 2012;85(1):59-73.
Petriz et al., "Proteomics applied to exercise physiology: a cutting-edge technology," *Cell Physiol.* 2012, 227(3):885-98.
Schlatter et al., "Generation, characterization and structural data of chymase binding proteins based on the human Fyn kinase SH3 domain," 2012, *MAbs*, vol. 4(4), 497-508.
Shackleton et al., "Heterogeneity in Cancer: Cancer Stem Cells versus Clonal Evolution," 2009, *Cell*, vol. 138(5), 822-829.
Singh et al., "Identification of human brain tumour initiating cells," 2004, *Nature*, vol. 432(7015), 396-401.
Tuschl, "RNA interference and small interfering RNAs," *Chembiochem.*, 2001, vol. 2(4), 239-245.
Venere et al., "Cancer stem cells in gliomas: Identifying and understanding the apex cell in cancer's hierarchy," 2011, *Glia, Special Issue: Glioma*, vol. 59(8), 1148-1154.
Zamore, "RNA interference: listening to the sound of silence," *Nat Struct Biol*, 2001, vol. 8(9), 746-750.
International Preliminary Report on Patentability for PCT/EP2013/077776, 8 pgs.
International Search Report for PCT/EP2013/077776, 3 pgs.
Exendin-4 data sheet (2 pages).
Hes3 (ID390992) Trilencer-27-Human siRNA data sheet (1 page).
Hes3 siRNA (h):sc-88003 data sheet (1 page).
Allen and Lobe, "A Comparison of Notch, HES and GRG Expression During Murine Embryonic and Post-Natal Development," *Cell Mol Biol*, 1999, 45(5):687-708.
Lino et al., "Notch Signaling in Glioblastoma: A Developmental Drug Target?" *BMC Med*, 2010; 8:72, doi: 10.1186/1741-7015-8-72.
Lobe, "Expression of the Helix-Loop-Helix Factor, Hes3, During Embryo Development Suggests a Role in Early Midbrain-Hindbrain Patterning," *Mech. Dev.*, 1997, 62(2):227-37.
Masjkur et al., "Hes3 is Expressed in the Adult Pancreatic Islet and Regulates Gene Expression, Cell Growth and Insulin Release," *J Biol Chem*, Dec. 19, 2014;289(51):33503-16, doi: 10.1074/jbc.M114.590687. Epub Nov. 4, 2014.
Sasai et al., "Two Mammalian Helix-Loop-Helix Factors Structurally Related to *Drosophila* Hairy and Enhancer of Split," *Genes Dev.* 1992; 6(12B):2620-34.
Wang et al., "Notch Signaling Proteins: Legitimate Targets for Cancer Therapy," *Curr Protein Pept Sci*, 2010; 11(6):398-408.
Yuan et al., "Notch Signaling: An Emerging Therapeutic Target for Cancer Treatment," *Cancer Lett*, Dec. 1, 2015; 369(1):20-7. doi: 10.1016/j.canlet.2015.07.048. Epub Sep. 1, 2015.

\* cited by examiner

MIN6 cells in culture:

1.1B4 cells in culture:

MANIPULATION OF HAIRY AND ENHANCER OF SPLIT 3 (HES3) AND ITS REGULATORS/MEDIATORS AS AN ANTI-CANCER STRATEGY

This application is the § 371 U.S. National Stage Entry of International Application No. PCT/EP2013/077776, filed Dec. 20, 2013, which claims priority to European Application No. 12199215.0, filed Dec. 21, 2012, each of which is incorporated by reference herein in its entirety.

The present invention relates to an inhibitor of Hairy and Enhancer of Split 3 (Hes3) for use in treating a tumour. The invention further relates to an in-vitro method for diagnosing a tumour, comprising determining the amount of Hes3 protein in a cerebrospinal fluid (CSF)-derived sample obtained from a subject, wherein an increased amount of Hes3 protein is indicative of the presence of a tumour.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Although many advances have been made in the treatment of cancer, the established anti-cancer therapies cannot always prevent the occurrence of relapse and metastasis. One obstacle in any cancer-therapy is that cancer cells often become resistant to anti-cancer treatments, for example, by up-regulating certain factors or by acquiring mutations that allow the cell to evade the effect of the treatment. Accordingly, the original treatment often will no longer affect these cells. In such cases, it may be necessary to make use of alternative treatments that target other pathways, factors or aspects required for the survival of the cancer cell (Chaffner and Weinberg, 2011). Another reason for the insufficient efficacy of established treatments, such as chemotherapy and radiotherapy, is that tumours contain cells that are resistant to the treatment and that have the ability to regenerate the tumour.

One of the groundbreaking developments in cancer biology over the last two decades is the understanding that the different cell populations within a tumour are not equal in their ability to regenerate the tumour. The cell population with the strongest ability to regenerate the tumour (in experimental settings) is termed the cancer stem cell (CSC) (Magee et al., 2012). CSCs, like other stem cells, are known to proliferate slowly and to enter long periods of quiescence in which they proliferate even more slowly or not at all. Therefore, CSCs are resistant to current therapies like chemotherapy and radiotherapy which are designed to target primarily fast-proliferating cells (Brunner et al., 2012).

A CSC, which persists even after treatment, may divide into two daughter cells of which one may again be a stem cell, whereas the other daughter cell may become a more differentiated cell which divides more quickly thereby increasing the size of the tumour.

Thus, therapies that target only differentiated tumour cells, but not CSCs, cannot eradicate a tumour because the remaining CSCs have the ability to regenerate the tumour and to lead to a relapse (Magee et al., 2012).

As a consequence, endeavours have been made to identify specific CSC markers and to establish CSC-specific therapies. One such example relates to the discovery that CD33 is widely expressed on the surface of leukemic stem cells (LSCs). This surface marker was found to be expressed on 80-90% of leukemic cells in patients suffering from acute myeloid leukemia (AML). Given its extensive expression on LCSs, an anti-CD33 antibody for the treatment of AML was developed. Subsequently, it was shown that the low density of CD33 on the cell surface prevented the significant induction of antibody- or complement-dependent cytotoxicity (Bakker et al., 2004). Accordingly, a combination of the anti-CD33 antibody with calicheamicin (a cytotoxic antibiotic) was developed and approved by the FDA in 2000 for the use in CD33+ AML patients who are 60 years of age or older and who are not candidates for other cytotoxic chemotherapy but are experiencing first relapse. This combination, which is referred to as Gemutuzumab ozogamacin (GO) or Mylotarg, was unfortunately found to lead to increased patient death without added benefits to the patients over conventional therapies and was therefore withdrawn in 2010 (Clayton and Mousa, 2011).

Another example is that of C-type lectin-like molecule-1 (CLL-1) which was identified as being highly expressed on the surface of LSCs but not of normal stem cells. In spite of the successful identification of CLL-1 as a marker of LSCs, there is not much evidence of its use as a therapeutic target to date (Clayton and Mousa, 2011).

An alternative approach to targeting CSCs via specific markers expressed on the cell surface is the use of inhibitors interfering with signalling pathways that are up-regulated in or specific to CSCs. Integrin linked kinase (ILK) was identified as a potential target because it is over-expressed, for example, in AML blast cells and is involved in the PI3K/Akt/mTOR pathway, a pathway that is often associated with survival and proliferative mechanisms utilized by malignant cells. The finding that ILK is highly expressed also in quiescent cells rendered it attractive as a potential target. When applied to cultured AML cells in vitro, the combination of the ILK inhibitor QLT0267 with the chemotherapeutic agents Ara-C or Daunorubicin yielded an additive or synergistic effect in most cases. However, in some cases, an antagonistic effect was observed which drastically reduced the attractiveness of ILK as a therapeutic target (Clayton and Mousa, 2011).

Furthermore, recent evidence shows that established biomarkers of CSCs may be inadequate for the prediction of the ability of a cell to form a tumour and/or a metastasis. For example, although the marker CD133 has been established as a CSC marker in several tumours, recent papers demonstrate that cells lacking expression of this marker are also able to form tumours, exhibiting CSC properties. Similar results have been obtained with additional markers, including CD271 and ABCB5 (Shackelton et al., 2009).

Androutsellis-Theotokis et al., 2010a found that the transcription factor Hes3 is expressed in CSCs. Further, Androutsellis-Theotokis et al., 2010b described that in these cells, in contrast to endogenous quiescent stem cells, Hes3 is present not only in the cytoplasm but also in the nucleus. However, neither of the two studies addressed the role of Hes3 for the survival or maintenance of CSCs.

Although many biomarkers that are indicative of the presence of tumours and CSCs have been identified, for example through the use of proteomic techniques, none of these markers has yet attained broad application in clinical diagnosis, prognosis, therapeutic target selection or molecular classification, especially in case of brain tumours. In some cases referred to above, initially promising markers have failed in practice. Furthermore, none of the markers identified so far seem to have been successfully used for targeting cancer stem cells.

Consequently, there is still a need for improved treatment options and developments towards treatment options that overcome these disadvantages. Critical to this effort is the identification of suitable biomarkers for the detection of tumours and especially of brain tumours for the use in diagnostic, prognostic (foretelling the course and/or outcome of the disease), and predictive (predicting the response to treatment) methods, and in particular markers that also provide conclusive evidence regarding the presence of CSCs.

This need is addressed by the provision of the embodiments characterised in the claims. Accordingly, the present invention relates to an inhibitor of Hairy and Enhancer of Split 3 (Hes3) for use in treating a tumour.

The following terms are all known in the art and are used in accordance with the definitions provided there. The definitions provided in this specification are solely intended to reflect the understanding of these terms in the art. Where nevertheless a discrepancy arises, the definitions provided herein supersede.

The term "Hes3" is an abbreviation of "Hairy and enhancer of split 3" and both terms are used interchangeably herein. Hes3 (also known as Class B basic helix-loop-helix protein 43 (bHLHb43), GeneID: 390992, GenBank accession no: NP_001019769.1, UniProtKB accession number: Q5TGS1) is a transcription factor. Expression of Hes3 was described to be induced if phosphorylation of Akt, mTOR and STAT3 (on serine 727 but not on tyrosine 705) is induced while JAK or p38 are not activated. Suitable ligands for inducing Hes3 expression include, but are not limited to, the Tie2 ligand angiopoietin2 (Ang2); the Notch ligands Dll4 and Jagged 1 (Jag1) and insulin (Androutsellis-Theotokis et al., 2006; Androutsellis-Theotokis et al., 2008; Androutsellis-Theotokis et al., 2009). The expression of Hes3 has further been shown in these studies to induce the expression of Sonic hedgehog (Shh) and to promote the survival of NSCs. Further, it was found that insulin and the Notch ligand Dll4 promote expansion of adult mouse subventricular zone NSC cultures and that the efficacy of this treatment is significantly reduced in Hes3 null cultures.

The term "inhibitor" designates a compound lowering, including completely abolishing (within the limits of detection) the activity of a target molecule, preferably by performing one or more of the following effects: (i) the transcription of the gene encoding the protein to be inhibited is lowered, (ii) the translation of the mRNA encoding the protein to be inhibited is lowered, (iii) the protein performs its biochemical function with lowered or abolished efficiency in presence of the inhibitor, and (iv) the protein performs its cellular function with lowered or abolished efficiency in presence of the inhibitor.

Compounds falling in class (i) include compounds interfering with the transcriptional machinery and/or its interaction with the promoter of said gene, with expression control elements remote from the promoter such as enhancers, and/or with components of upstream pathways that initiate or enhance the transcription of the target gene. This may include, for example, oligonucleotides that interfere with the binding of a transcription factor (see e.g. Carbone et al., 2003) or compounds that are directed against an upstream factor required for the transcription of the target, such as a component of a pathway that induces the transcription of the target. Compounds of class (ii) comprise antisense constructs and constructs for performing RNA interference (e.g. siRNA, shRNA, miRNA) well known in the art (see, e.g. Tuschl, 2001; Zamore, 2001). Compounds of class (iii) interfere with the molecular function of the protein to be inhibited, in the present case of a transcription factor with its ability to translocate to the nucleus, to bind DNA and/or to act as a transcriptional activator or repressor as well as/or with its ability to promote survival of stem cells and/or to prevent their differentiation. In particular, compounds targeting the nuclear or mitochondrial localisations signals, the bHLH-domain or the phosphorylation sites on Hes3 are envisioned. Based on the amino acid sequence of Hes3 several residues (including 8 serine residues and a threonine residue) are predicted to be phosphorylated. Methods for identifying phosphorylation sites and for verifying putative phosphorylation sites predicted by bioinformatic means are well known in the art. Class (iv) includes compounds which do not necessarily bind directly to Hes3, but still interfere with its activity, for example by binding to and/or inhibiting the function or expression of members of a pathway which comprises Hes3. These members may be either upstream or downstream of Hes3 within said pathway. As non-limiting examples, Akt or mTOR activation or activity, STAT3 phosphorylation on serine 727, or the secretion of Shh or its interaction with its receptor may be inhibited.

The determination of binding of potential inhibitors can be effected in, for example, any binding assay, preferably biophysical binding assay, which may be used to identify binding test molecules prior to performing the functional/activity assay with the inhibitor. Suitable biophysical binding assays are known in the art and comprise fluorescence polarization (FP) assay, fluorescence resonance energy transfer (FRET) assay and surface plasmon resonance (SPR) assay.

In accordance with the invention, the level of activity of Hes3 in the presence of the inhibitor is less than 90%, more preferred less than 80%, less than 70%, less than 60% or less than 50% of the activity of Hes3 in absence of the inhibitor. Yet more preferred are inhibitors lowering the level to less than 25%, less than 10%, less than 5% or less than 1% of the activity of Hes3 in absence of the inhibitor. The term activity, as used herein, denotes in particular any known biological activity of Hes3 or any combination thereof including functions elucidated in accordance with the present invention. Examples of said biological function are the activity as a transcription factor, and the ability to promote the survival of cancer stem cells.

The efficiency of the inhibitor can be quantified by comparing the level of activity of Hes3 in the presence of the inhibitor to that in the absence of the inhibitor. For example, as an activity measure may be used: the change in amount of mRNA formed; the change in amount of protein formed; the change in the expression of Hes3 target genes, such as for example Shh, on the mRNA or protein level; the expression of a reporter gene, such as luciferase or GFP, under the control of the promoter of a known Hes3 target gene, such as for example Shh; and/or the change in the cellular phenotype or in the phenotype of an organism.

In cases where the inhibitor acts by affecting the expression level of Hes3 or an activator thereof, as in case of inhibitors belonging to classes (i), (ii) or potentially (iv) above, the determination of the expression level of the target can, for example, be carried out on the nucleic acid level or on the amino acid level.

Methods for determining the expression of a protein on the nucleic acid level include, but are not limited to, northern blotting, PCR, RT-PCR or real RT-PCR. PCR is well known in the art and is employed to make large numbers of copies of a target sequence. The PCR, generally, consists of many repetitions of a cycle which consists of: (a) a denaturing step (b) an annealing step and (c) an extension step. It is well known in the art how to optimise PCR conditions by adjusting the duration and temperature of the different steps for the amplification of specific nucleic acid molecules with primers of different length and/or composition. Generally, PCR can be performed, for example, in a 50 µl reaction mixture containing PCR buffer, deoxynucleoside triphosphates, primers, template DNA and a polymerase. Suitable amounts and concentrations of the different components are well known in the art and it is also known how to adjust the reaction to the particular purpose by scaling down or increasing the volume of the reaction mix, by changing the concentration of particular compounds and/or by including additional ingredients. Suitable polymerases for use with a DNA template include, for example, *E. coli* DNA polymerase I or its Klenow fragment, T4 DNA polymerase, Tth polymerase, Taq polymerase, a heat-stable DNA polymerase isolated from *Thermus aquaticus* Vent, Amplitaq, Pfu and KOD, some of which may exhibit proof-reading function and/or different temperature optima.

The "reverse transcriptase polymerase chain reaction" (RT-PCR) is used when the nucleic acid to be amplified consists of RNA. The term "reverse transcriptase" refers to an enzyme that catalyzes the polymerization of deoxyribonucleoside triphosphates to form primer extension products that are complementary to a ribonucleic acid template. Following the generation of a complementary, copy-DNA (cDNA), the genomic RNA/cDNA duplex template typically is heat denatured during the first denaturation step after the initial reverse transcription step leaving the DNA strand available as an amplification template. The conditions for reverse transcription and subsequent amplification of the cDNA are well known in the art and can be adjusted according to the needs of the particular case for example by changing incubation temperatures or duration or by increasing or decreasing the concentrations of one or several components of the reaction mix.

The resulting products are typically loaded onto an agarose gel and band intensities are compared after staining the nucleic acid molecules with an intercalating dye such as ethidium bromide or SybrGreen. A lower band intensity of the sample treated with the inhibitor as compared to a non-treated sample indicates that the inhibitor successfully inhibits the expression of the protein on the nucleic acid level.

Real-time PCR employs a specific probe, in the art also referred to as TaqMan probe, which has a reporter dye covalently attached at the 5' end and a quencher at the 3' end. After the TaqMan probe has been hybridized in the annealing step of the PCR reaction to the complementary site of the polynucleotide being amplified, the 5' fluorophore is cleaved by the 5' nuclease activity of Taq polymerase in the extension phase of the PCR reaction. This enhances the fluorescence of the 5' donor, which was formerly quenched due to the close proximity to the 3' acceptor in the TaqMan probe sequence. Thereby, the process of amplification can be monitored directly and in real time, which permits a significantly more precise determination of expression levels than conventional end-point PCR. Also of use in Real time RT-PCR experiments is a DNA intercalating dye such as SybrGreen for monitoring the de novo synthesis of double stranded DNA molecules.

Methods for the determination of the expression of a protein on the amino acid level include but are not limited to western blotting or polyacrylamide gel electrophoresis in conjunction with protein staining techniques such as Coomassie Brilliant blue or silver-staining. The total protein is loaded onto a polyacrylamide gel and electrophoresed. Afterwards, the separated proteins are transferred onto a membrane, e.g. a polyvinyldifluoride (PVDF) membrane, by applying an electrical current. The proteins on the membrane are exposed to an antibody specifically recognizing the protein of interest. After washing, a second antibody specifically recognizing the first antibody and carrying a readout system such as a fluorescent dye is applied. The amount of the protein of interest is determined by comparing the fluorescence intensity of the protein derived from the sample treated with the inhibitor and the protein derived from a non-treated sample. A lower fluorescence intensity of the protein derived from the sample treated with the inhibitor indicates a successful inhibitor of the protein. Also of use in protein quantification is the Agilent Bioanalyzer technique.

Alternatively, the amount of protein could be determined by Enzyme-linked Immunosorbent Assay (ELISA) or by analysis by intracellular fluorescence activated cell sorting (FACS). To determine the amount of protein by ELISA, the sample with an unknown amount of protein (antigen) is immobilized using a specific antibody on a solid support. Afterwards, the detection antibody, which can be linked to an enzyme, is added, forming a complex with the antigen. In case the detection antibody is not linked to an enzyme it can in turn be detected by a secondary antibody that is conjugated to an enzyme. Between the individual steps, any proteins or antibodies that are not specifically bound are removed by washing with a mild detergent solution. Finally, a substrate that allows the visualization and quantitation of the enzymatic reaction catalyzed by the enzyme is added. The correlation between signal intensity and amount of antigen is used to determine the unknown amount of protein.

Similarly, the efficiency of the inhibitor, independently of the class it belongs to, with the exception of inhibitors that target components that are downstream of Hes3 and/or its targets, can be quantified by comparing the amount of Shh and/or other targets of Hes3 on the mRNA or protein level in the presence of the inhibitor to that in the absence of the inhibitor. Alternatively, the efficacy of the inhibitor can be assessed or by determining the expression of a reporter gene, such as luciferase or GFP, under the control of the Shh promoter, in presence or absence of the inhibitor, wherein a reduction in the expression of the reporter gene in the presence of or after administration of the inhibitor as compared to the expression in the absence of or prior to said administration is indicative of a successful inhibition of the ability of Hes3 to act as a transcription factor. Methods for determining the expression of a factor on mRNA- or protein-level are described above.

The efficiency of inhibitors, especially inhibitors of class (iii), can further by assessed by analysing the subcellular localisation of Hes3 in presence versus absence of the inhibitor. The subcellular localisation of Hes3 can be assessed by immunocytochemical analysis or by the use of cell lines transfected with a GFP-fused Hes3 construct. Methods for immunocytochemical analysis are well known in the art and are described, for example, in Immunocytochemistry Methods and Protocols, edited by Lorette C. Javois, 2nd edition, 1999. Human Press or on the world wide web (www) under de-de.invitrogen.com/site/de/de/home/References/Molecular-Probes-The-Handbook.html.

Alternatively, a change in the phenotype of a cell or an organism can be taken as a measure for the efficacy of the inhibitor. This includes, for example, a change to the morphology of the cell, a reduction in the expression of biomarkers associated with CSCs, such as for example, prominin, nestin, sox2 or Hes3, or in the number of CSCs in the presence of the inhibitor as compared to the number of CSCs in the absence of the inhibitor. A reduction in the expression of CSC-specific biomarkers can be assessed, for example, by immunocytochemistry or FACS analysis.

The function of any of the inhibitors referred to in the present invention may be identified and/or verified by using high throughput screening assays (HTS). High-throughput assays, independently of being biochemical, cellular or other assays, generally may be performed in wells of microtiter plates, wherein each plate may contain, for example 96, 384 or 1536 wells. Handling of the plates, including incubation at temperatures other than ambient temperature, and bringing into contact of test compounds with the assay mixture is preferably effected by one or more computer-controlled robotic systems including pipetting devices. In case large libraries of test compounds are to be screened and/or screening is to be effected within short time, mixtures of, for example 10, 20, 30, 40, 50 or 100 test compounds may be added to each well. In case a well exhibits biological activity, said mixture of test compounds may be de-convoluted to identify the one or more test compounds in said mixture giving rise to the observed biological activity.

The term "tumour", also referred to as cancer herein, relates to an abnormal cellular mass that is generated by the uncontrolled growth or proliferation of cells. The term includes primary growths as well as secondary tumours, also referred to as metastases, that are derived from a primary tumour but are no longer associated with this original growth. These secondary tumours may be located in the same or adjacent tissue as the primary tumour or at a distant site. Tumours are abnormal cell growths that are, or are associated with, for example, acute lymphoblastic leukemia, acute myeloid leukemia, adrenocortical carcinoma, anal cancer, appendix cancer, cerebellar astrocytoma, cerebral astrocytoma, basal cell carcinoma, bile duct cancer, extrahepatic bladder cancer, bone cancer, osteosarcoma/malignant fibrous histiocytoma, brainstem glioma, brain cancer, malignant glioma, ependymoma, medulloblastoma, supratentorial primitive neuroectodermal tumours, visual pathway and hypothalamic glioma, breast cancer, bronchial adenomas/carcinoids/carcinoids, Burkitt lymphoma, carcinoid tumours, primary central nervous system lymphoma, cervical cancer, chronic lymphocytic leukemia, chronic myelogenous leukemia, chronic myeloproliferative disorders, colon cancer, cutaneous T-cell lymphoma, desmoplastic small round cell tumours, endometrial cancer, esophageal cancer, Erwing's sarcoma, extrahepatic bile duct cancer, intraocular melanoma, retinoblastoma, gallbladder cancer, gastric cancer, gastrointestinal carcinoid tumours, gastrointestinal stromal tumours (GIST), extracranial, extragonadal, or ovarian germ cell tumours, gestational trophoblastic tumors, hairy cell leukemia, head and neck cancer, hepatocellular cancer, Hodgkin lymphoma, hypopharyngeal cancer, islet cell carcinoma (endocrine pancreas), Kaposi sarcoma, renal cell cancer, laryngeal cancer, lip and oral cavity cancer, liposarcoma, non-small cell lung cancer, small cell lung cancer, non-Hodgkin's lymphoma, macroglobulinemia, malignant fibrous histiocytoma of bone/osteosarcoma, melanoma, Merkel cell carcinoma, malignant mesothelioma, metastatic squamous neck cancer with occult primary tumour, multiple endocrine neoplasia syndrome, multiple myeloma/plasma cell neoplasm, myelodysplastic/myeloproliferative diseases, chronic myelogneous leukemia, nasopharyngeal carcinoma, neuroblastoma, oropharyngeal cancer, ovarian cancer, ovarian epithelial cancer, pancreatic cancer, paranasal sinus and nasal cavity cancer, parathyroid cancer, pharyngeal cancer, pheochromocytoma, pineal astrocytoma, pineal germinoma, pineoblastoma and supratentorial primitive neuroectodermal tumours, pituitary adenoma, pleuropulmonary blastoma, primary central nervous system lymphoma, prostate cancer, rectal cancer, rhabdomyosarcoma, salivary gland cancer, soft tissue sarcoma, uterine sarcoma, Sézary syndrome, skin cancer (non-melanoma), squamous cell carcinoma, thymoma, thymic carcinoma, thyroid cancer, urethral cancer, endometrial uterine cancer, uterine sarcoma, vaginal cancer, and vulvar cancer.

Preferably, tumours to be treated with a Hes3 inhibitor are tumours arising in tissues which normally express Hes3. For example, brain tumours, especially the most aggressive tumours like glioblastoma multiforme which are thought to contain immature cells. Pancreatic tumours and adrenal tumours may also be well suited as these tissues express Hes3. Skin tumours may also be well suited because skin and neural tissue are derived from neuroectoderm and may, therefore, share common mechanisms that regulate and maintain Hes3 expression. Haematopoietic tumours are also interesting as Hes3 expression is found in blood cells. Most preferably, the tumours are meningioma I or glioblastoma multiforme grade IV.

The inhibitor used in accordance with the present invention serves the purpose of reducing tumour burden or of eradicating the tumour, including the CSCs. To this end, the inhibitor may be administered to a subject in need thereof, e.g. in form of a pharmaceutical composition. The pharmaceutical composition may, optionally, comprise further molecules capable of altering the characteristics of the inhibitor thereby, for example, stabilizing, modulating and/or activating its function. The composition may be in solid, liquid or gaseous form and may be, inter alia, in the form of (a) powder(s), (a) tablet(s), (a) solution(s) or (an) aerosol(s). The pharmaceutical composition of the present invention may, optionally and additionally, comprise a pharmaceutically acceptable carrier. Examples of suitable pharmaceutical carriers are well known in the art and include phosphate buffered saline solutions, water, emulsions, such as oil/water emulsions, various types of wetting agents, sterile solutions, organic solvents including DMSO etc. Compositions comprising such carriers can be formulated by well known conventional methods. Administration of these pharmaceutical compositions may occur orally, rectally, intrathecally, parenterally, intracisternally, intravaginally, intraperitoneally, topically (as by powders, ointments, drops or transdermal patch), bucally, or as an oral or nasal spray to a subject at a suitable dose.

The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. The therapeutically effective amount for a given situation will readily be determined by routine experimentation and is within the skills and judgement of the ordinary clinician or physician. Generally, the regimen as a regular administration of the pharmaceutical composition should be in the range of 1 µg to 5 g units per day. However, a more preferred dosage might be in the range of 0.01 mg to 100 mg, even more preferably 0.01 mg to 50 mg and most preferably 0.01 mg to 10 mg per day.

Furthermore, if for example said compound is an iRNA agent, such as an siRNA, the total pharmaceutically effective amount of pharmaceutical composition administered will typically be less than about 75 mg per kg of body weight, such as for example less than about 70, 60, 50, 40, 30, 20, 10, 5, 2, 1, 0.5, 0.1, 0.05, 0.01, 0.005, 0.001, or 0.0005 mg per kg of body weight. More preferably, the amount will be less than 2000 nmol of iRNA agent per kg of body weight, such as for example less than 1500, 750, 300, 150, 75, 15, 7.5, 1.5, 0.75, 0.15, 0.075, 0.015, 0.0075, 0.0015, 0.00075 or 0.00015 nmol of iRNA agent per kg of body weight. However, it is also preferred that the total pharmaceutically effective amount of pharmaceutical composition administered is at least 0.0001 mg iRNA agent per kg of body weight. Also preferred is that the amount is at least 0.000075 nmol of iRNA agent per kg of body weight. The length of treatment needed to observe changes and the interval following treatment for responses to occur vary depending on the desired effect. The particular amounts may be determined by conventional tests which are well known to the person skilled in the art.

Preferably, said subject is a vertebrate and more preferably a mammal. Even more preferably, the mammal is selected from a group comprising horses, cattle, pigs, sheep, goats, dogs, cats, rodents or primates. Yet more preferably, the mammal is a rodent or a non-human primate and most preferably a human.

In accordance with the present invention, "reducing the tumour burden" means a statistically significant lowering of tumour size or tumour mass and/or the degree of invasion. Preferably, tumour size or tumour mass and/or the degree of invasion are lowered more than 20%, more than 30%, more than 40% or more than 50%. Yet more preferred is a reduction of tumour mass by more than 75%, more than 90%, more than 95%, more than 99% and most preferably by 100%. This reduction can be assessed by imaging techniques, such as computed tomography (CT), positron emission tomography (PET) scans or magnetic resonance imaging (MRI) or by measuring the expression of biomarkers associated with tumour cells or CSCs.

In accordance with the present invention, it was surprisingly found that Hes3 is required for the survival and maintenance of CSCs and is therefore a suitable target in anti-tumour therapy which, by targeting CSCs which are resistant to conventional therapies and which can lead to the regeneration of tumours and relapses, overcomes a major disadvantage of established therapies.

The relevance of Hes3 for the survival of CSCs is surprising for a number of reasons. Firstly, it is well known in the art that the activity of a specific pathway in a certain cell type does not mean that this pathway is essential for the survival of this cell. While many pathways contribute to the growth and survival of cells, only a few are truly essential. This is, amongst other reasons, due to a certain redundancy between different pathways and/or components thereof. In case of Hes3 it was shown that the loss of one gene of the Hes/Hey family can be compensated by other family members (Hirata et al., 2001, Hatakeyama et al., 2004). This may be the reason why mice in which Hes3 has been genetically deleted show no overt phenotype. On these grounds it would have been expected that upon inhibition of Hes3 other factors would substitute for the loss of this protein.

Further, as experience regarding other CSC-markers has shown, the mere presence of a protein on or in a cell does not necessarily make it a viable target for anti-tumour treatments. Apart from the potential redundancies as discussed above, this may be due, at least in part, to the well established fact that cancer cells often harbour mutations that render them independent of specific survival and growth pathways or certain components thereof. Accordingly, a factor that is required for the survival of a normal cell may therefore no longer be essential in the corresponding cancer cell.

So far, no anti-cancer treatment based on the inhibition of Hes3 has been described.

Accordingly, the present invention provides a novel target for use in cancer-treatment. The inhibitor used in accordance with the present invention is hence expected to become a useful alternative in the treatment of cancer, especially in cases where acquired resistance makes the treatment with conventional therapies impossible. Further, the present invention not only describes an improved inhibitor for treating tumours but also provides the first CSC-specific treatment and, thus, has the advantage over established therapies of reducing or eliminating the CSCs, which are the cells with the greatest ability to regenerate the tumour. Thus, inhibitors used in accordance with the present invention overcome a major disadvantage of established anti-tumour therapeutics.

In a preferred embodiment of the present invention, the inhibitor is selected from the group consisting of proteins, peptides, aptamers, siRNAs, shRNAs, miRNAs, ribozymes, antisense nucleic acid molecules, or small molecules.

The term "protein" as used herein refers to any high molecular mass compound consisting of one or more linear chains of the 20 amino acids of the genetic code joined by peptide bonds, occurring in living systems. The term "peptide" as used herein describes a group of molecules consisting of up to 30 amino acids, whereas "proteins" consist of more than 30 amino acids. Peptides and proteins may further form dimers, trimers and higher oligomers, i.e. consisting of more than one molecule which may be identical or non-identical. The corresponding higher order structures are, consequently, termed homo- or heterodimers, homo- or heterotrimers etc. The terms "peptide" and "polypeptide" (wherein "polypeptide" is interchangeably used with "protein") also refer to naturally modified peptides/proteins wherein the modification is effected e.g. by glycosylation, acetylation, phosphorylation and the like. Such modifications are well-known in the art. Proteins can be soluble in aqueous solvents, like enzymes such as kinases, proteases, phosphatases, oxidases and reductases as well as non-enzyme soluble proteins. Preferred soluble proteins are antibodies. The term "antibody" as used in accordance with the present invention comprises, for example, polyclonal or monoclonal antibodies. Furthermore, also derivatives or fragments thereof, which still retain the binding specificity, are comprised in the term "antibody". Antibody fragments or derivatives comprise, inter alia, Fab or Fab' fragments, Fd, F(ab')$_2$, Fv or scFv fragments, single domain V$_H$ or V-like domains, such as VhH or V-NAR-domains, as well as multimeric formats such as minibodies, diabodies, tribodies, tetrabodies or chemically conjugated Fab'-multimers (see, for example, Altshuler et al., 2010. Holliger and Hudson, 2005). The term "antibody" also includes embodiments such as chimeric (human constant domain, non-human variable domain), single chain and humanized (human antibody with the exception of non-human CDRs) antibodies.

Various techniques for the production of antibodies and fragments thereof are well known in the art and described, e.g. in Altshuler et al., 2010. Thus, polyclonal antibodies can be obtained from the blood of an animal following immunisation with an antigen in mixture with additives and adjuvans and monoclonal antibodies can be produced by any technique which provides antibodies produced by continuous cell line cultures. Examples for such techniques are described, e.g. Harlow and Lane (1988) and (1999) and include the hybridoma technique originally described by Köhler and Milstein, 1975, the trioma technique, the human B-cell hybridoma technique (see e.g. Kozbor, 1983; Li et al., 2006) and the EBV-hybridoma technique to produce human monoclonal antibodies (Cole et al., 1985). Furthermore, recombinant antibodies may be obtained from monoclonal antibodies or can be prepared de novo using various display methods such as phage, ribosomal, mRNA, or cell display. A suitable system for the expression of the recombinant (humanized) antibodies or fragments thereof may be selected from, for example, bacteria, yeast, insects, mammalian cell lines or transgenic animals or plants (see, e.g., U.S. Pat. No. 6,080,560; Holliger and Hudson, 2005). Further, techniques described for the production of single chain antibodies (see, inter alia, U.S. Pat. No. 4,946,778) can be adapted to produce single chain antibodies specific for the target of this invention. Surface plasmon resonance as employed in the BIAcore system can be used to increase the efficiency of phage antibodies.

Proteins can also be alternative binding proteins in which specific binding properties have been introduced, for example by mutagenesis, into a protein scaffold with suitable biophysical properties. Ideally, small globular proteins, that are easy to express and purify, that are soluble, stable, do not aggregate and that are non-immunogenic, are used as a scaffold. So far more than 50 proteins of this class have been described, among them affibodies, which are based on the Z-domain of staphylococcal protein A, Kunitz type domains, Adnectins (based on the tenth domain of human fibronectin), Anticalins (derived from lipocalins), DARPins (derived from ankyrin repeat proteins), avimers (based on multimerised Low Density Lipoprotein Receptor (LDLR)-A) and Fynomers® which are derived from the human Fyn SH3 domain (see e.g. Schlatter et al., 2012). Further, proteins can be membrane proteins, comprising peripheral membrane proteins and integral membrane proteins. Examples of membrane proteins include transporters, pores and receptors such as growth factor receptors, G-protein coupled receptors (GPCR) and receptors with seven, but also with less or more than seven transmembrane helices, or beta sheets. In addition, proteins can be single-domain proteins as well as multi-domain proteins and single chain as well as multiple chain proteins. Further embraced are embodiments, wherein the protein functions as part of a metabolic pathway and/or a signal transduction pathway. The protein may consist of or comprise protein domains known to function in signal transduction and/or known to be involved in protein-protein interaction. Further information about protein domains is available from the databases InterPro (see the world wide web at ebi.ac.uk/interpro/, Mulder et al., 2003), Pfam world wide web at sanger.ac.uk/Software/Pfam/, Bateman et al., 2004) and SMART (see the world wide web at smart.embl-heidelberg.de/, Letunic et al., 2004).

Preferred proteins according to the present invention include, for example, cytokines, agonistic antibodies or other proteins that lead to the activation of the JAK pathway and thereby indirectly to an inactivation of Hes3. This mode of indirect inhibition is based on the finding that Hes3 expression is enhanced by signalling pathways that induce STAT3-serine phosphorylation but suppressed by signals that induce both STAT-serine phosphorylation and the activation of JAK kinase (Androutsellis-Theotokis et al., 2006). Alternatively, soluble receptors or antibodies binding to ligands that lead to the expression of Hes3, or that interact with downstream effectors of Hes3 such as for example Shh, could be used to prevent the effects of these ligands or effectors and to indirectly inhibit Hes3. Furthermore, inactive or dominant negative forms of components of pathways leading to the expression of Hes3 such as, for example, STAT3 that cannot be phosphorylated on serine or that has constitutive phosphorylation on tyrosine or a modification mimicking such a tyrosine phosphorylation are envisioned. The same applies to inactive or dominant negative forms of required interaction partners or co-factors of Hes3. These proteins may be used directly, for example in complexes with other proteins or chemicals that allow them to diffuse through the plasma membrane into the cell, or may be brought into the target cell or organism in the form of nucleic acids encoding the respective protein.

Aptamers are nucleic acid molecules or peptide molecules that bind a specific target molecule. Aptamers are usually created by selecting them from a large random sequence pool, but natural aptamers also exist in riboswitches. Aptamers can be used for both basic research and clinical purposes as macromolecular drugs. Aptamers can be combined with ribozymes to self-cleave in the presence of their target molecule. These compound molecules have additional research, industrial and clinical applications (Osborne, 1997, Stull & Szoka, 1995).

More specifically, aptamers can be classified as nucleic acid aptamers, such as DNA or RNA aptamers, or peptide aptamers. Whereas the former normally consist of (usually short) strands of oligonucleotides, the latter preferably consist of a short variable peptide domain, attached at both ends to a protein scaffold.

Nucleic acid aptamers are nucleic acid species that, as a rule, have been engineered through repeated rounds of in vitro selection or equivalently, SELEX (systematic evolution of ligands by exponential enrichment) to bind to various molecular targets such as small molecules, proteins, nucleic acids, and even cells, tissues and organisms. This class of aptamers also includes the group of aptamers generated on the basis of L-RNA or L-DNA, which are termed spiegelmers.

Peptide aptamers usually are peptides or proteins that are designed to interfere with other protein interactions inside cells. They consist of a variable peptide loop attached at both ends to a protein scaffold. This double structural constraint greatly increases the binding affinity of the peptide aptamer to levels comparable to an antibody's (nanomolar range). The variable peptide loop typically comprises 10 to 20 amino acids, and the scaffold may be any protein having good solubility properties. Currently, the bacterial protein Thioredoxin-A is the most commonly used scaffold protein, the variable peptide loop being inserted within the redox-active site, which is a -Cys-Gly-Pro-Cys-loop in the wild protein, the two cysteins lateral chains being able to form a disulfide bridge. Peptide aptamer selection can be made using different systems, but the most widely used is currently the yeast two-hybrid system.

Aptamers offer the utility for biotechnological and therapeutic applications as they offer molecular recognition properties that rival those of the commonly used biomolecules, in particular antibodies. In addition to their discriminate recognition, aptamers offer advantages over antibodies as they can be engineered completely in a test tube, are readily produced by chemical synthesis, possess desirable storage properties, and elicit little or no immunogenicity in therapeutic applications. Non-modified aptamers are cleared rapidly from the bloodstream, with a half-life of minutes to hours, mainly due to nuclease degradation and clearance from the body by the kidneys, a result of the aptamer's inherently low molecular weight. Unmodified aptamer applications currently focus on treating transient conditions such as blood clotting, or treating organs such as the eye where local delivery is possible. This rapid clearance can be an advantage in applications such as in vivo diagnostic imaging. Several modifications, such as 2'-fluorine-substituted pyrimidines, polyethylene glycol (PEG) linkage, fusion to albumin or other half life extending proteins etc. are available to scientists such that the half-life of aptamers can be increased for several days or even weeks.

In accordance with the present invention, the term "small interfering RNA (siRNA)", also known as short interfering RNA or silencing RNA, refers to a class of 18 to 30, preferably 19 to 25, most preferred 21 to 23 or even more preferably 21 nucleotide-long RNA molecules, forming duplexes, i.e. double-stranded parts created by association of complementary sequences of two RNA strands, of at least 19 nucleotides, that play a variety of roles in biology. Most notably, siRNA is involved in the RNA interference (RNAi) pathway where the siRNA interferes with the expression of a specific gene. In addition to their role in the RNAi pathway, siRNAs also act in RNAi-related pathways, e.g. as an antiviral mechanism or in shaping the chromatin structure of a genome.

siRNAs naturally found in nature have a well defined structure: a short double-strand of RNA (dsRNA) with 2-nt 3' overhangs on either end. Each strand has a 5' phosphate group and a 3' hydroxyl (—OH) group. This structure is the result of processing by dicer, an enzyme that converts either long dsRNAs or small hairpin RNAs into siRNAs. siRNAs can also be exogenously (artificially) introduced into cells to bring about the specific knockdown of a gene of interest. Essentially any gene of which the sequence is known can thus be targeted based on sequence complementarity with an appropriately tailored siRNA. The double-stranded RNA molecule or a metabolic processing product thereof is capable of mediating target-specific nucleic acid modifications, particularly RNA interference and/or DNA methylation. Exogenously introduced siRNAs may be devoid of overhangs at their 3' and 5' ends, however, it is preferred that at least one RNA strand has a 5'- and/or 3'-overhang. Preferably, one end of the double-strand has a 3'-overhang from 1-5 nucleotides, more preferably from 1-3 nucleotides and most preferably 2 nucleotides. The other end may be blunt-ended or has up to 6 nucleotides 3'-overhang. In general, any RNA molecule suitable to act as siRNA is envisioned in the present invention. The most efficient silencing was so far obtained with siRNAs in which the sense and the antisense strand are complementary to each other in 19 nt,so that a duplex of 19 nt with 2-nt 3'-overhangs is formed. The sequence of the 2-nt 3' overhang makes a small contribution to the specificity of target recognition restricted to the unpaired nucleotide adjacent to the first base pair (Elbashir et al. 2001). 2'-deoxynucleotides in the 3' overhangs are as efficient as ribonucleotides, but are often cheaper to synthesize and probably more nuclease resistant. siRNAs to be used in the present invention are preferably chemically synthesized using appropriately protected ribonucleoside phosphoramidites and a conventional DNA/RNA synthesizer. Suppliers of RNA synthesis reagents include Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK). Most conveniently, siRNAs or shRNAs are obtained from commercial RNA oligo synthesis suppliers, which sell RNA-synthesis products of different quality and costs. In general, the RNAs applicable in the present invention are conventionally synthesized and are readily provided in a quality suitable for RNAi.

Delivery of siRNA may be accomplished using any of the methods known in the art, for example by combining the siRNA with saline and administering the combination intravenously or intranasally or by formulating siRNA in glucose (such as for example 5% glucose) or cationic lipids and polymers can be used for siRNA delivery in vivo through systemic routes either intravenously (IV) or intraperitoneally (IP) (Fougerolles, 2008; Lu and Woodle, 2008, Gavrilov and Salzmann, 2012)

Preferred siRNAs are Hes3 siRNA sc88003 obtainable from Santa Cruz Biotechnology or Hes3 siRNAs SR318208A and SR318208C from OriGene Tech.

A short hairpin RNA (shRNA) is a sequence of RNA that makes a tight hairpin turn that can be used to silence gene expression via RNA interference. shRNA uses a vector introduced into cells and utilizes the U6 promoter to ensure that the shRNA is always expressed. This vector is usually passed on to daughter cells, allowing the gene silencing to be inherited. The shRNA hairpin structure is cleaved by the cellular machinery into siRNA, which then promotes the specific knockdown of a gene of interest as described above. Routes of non-viral delivery of shRNAs include, for example, the methods described for the delivery of siRNA above.

The term "miRNA" as used herein refers to microRNAs, which are single-stranded RNA molecules of about 21-23 nucleotides in length, which regulate gene expression. miRNAs are encoded by genes that are transcribed from DNA but not translated into protein (non-coding RNA); instead they are processed from primary transcripts known as pri-miRNA to short stem-loop structures called precursor or pre-miRNA and finally to functional miRNA. Mature miRNA molecules are partially complementary to one or more messenger RNA (mRNA) molecules, and their main function is to downregulate gene expression. Animal miRNAs are usually complementary to a site in the 3' UTR whereas plant miRNAs are usually complementary to coding regions of mRNAs. Initial studies have indicated that miRNAs regulate gene expression post-transcriptionally at the level of translational inhibition at P-bodies in the cytoplasm. However, miRNAs may also guide mRNA cleavage in a manner similar to siRNAs.

miRNAs typically differ from siRNA because they are processed from single stranded RNA precursors and show only partial complementarity to mRNA targets. They have been implicated in a wide range of functions such as cell growth and apoptosis, development, neuronal plasticity and remodeling, and even insulin secretion. miRNA can also be used to silence gene expression via RNA interference.

A ribozyme (from ribonucleic acid enzyme, also called RNA enzyme or catalytic RNA) is an RNA molecule that catalyzes a chemical reaction. Many natural ribozymes catalyze either their own cleavage or the cleavage of other RNAs, but they have also been found to catalyze the aminotransferase activity of the ribosome. Non-limiting examples of well-characterized small self-cleaving RNAs are the hammerhead, hairpin, hepatitis delta virus, and in-vitro-selected lead-dependent ribozymes, whereas the group I intron is an example for larger ribozymes. The principle of catalytic self-cleavage is well established. The hammerhead ribozymes are characterized best among the RNA molecules with ribozyme activity. Since it was shown that hammerhead structures can be integrated into heterologous RNA sequences and that ribozyme activity can thereby be transferred to these molecules, it appears that catalytic antisense sequences for almost any target sequence can be created, provided the target sequence contains a potential matching cleavage site. The basic principle of constructing hammerhead ribozymes is as follows: An interesting region of the RNA, which contains the GUC (or CUC) triplet, is selected. Two oligonucleotide strands, each usually with 6 to 8 nucleotides, are taken and the catalytic hammerhead sequence is inserted between them. Molecules of this type were synthesized for numerous target sequences. They showed catalytic activity in vitro and in some cases also in vivo. The best results are usually obtained with short ribozymes and target sequences.

A recent development, also useful in accordance with the present invention, is the combination of an aptamer recognizing a small compound with a hammerhead ribozyme. The conformational change induced in the aptamer upon binding the target molecule is supposed to regulate the catalytic function of the ribozyme.

The term "antisense nucleic acid molecule" is known in the art and refers to a nucleic acid which is complementary to a target nucleic acid. An antisense molecule in accordance with the invention is capable of interacting with the target nucleic acid, more specifically it is capable of hybridizing with the target nucleic acid. Due to the formation of the hybrid, transcription of the target gene(s) and/or translation of the target mRNA is reduced or blocked (see for example Fattal and Barratt, 2009). Standard methods relating to antisense technology have been described (see, e.g., Melani et al., 1991).

A "small molecule" according to the present invention may be, for example, an organic molecule. Organic compounds can be natural or synthetic. Alternatively, the "small molecule" in accordance with the present invention may be an inorganic compound. Inorganic compounds are derived from mineral sources and include all compounds without carbon atoms (except carbon dioxide, carbon monoxide and carbonates). Preferably, the small molecule has a molecular weight of less than about 2000 amu, or less than about 1000 amu such as less than about 500 amu, and even more preferably less than about 250 amu. Small molecules in accordance with the present invention typically have a molecular weight of at least 50 amu, preferably at least 100 amu. The size of a small molecule can be determined by methods well-known in the art, e.g., mass spectrometry. The small molecules may be designed, for example, based on the crystal structure of the target molecule, where sites presumably responsible for the biological activity, can be identified and verified in in-vivo assays such as in-vivo high-throughput screening (HTS) assays.

The terms "protein", "peptide", "aptamer", "siRNA", "shRNA", "miRNA", "ribozyme", "antisense nucleic acid molecule" or "small molecule" as used herein also refer to the inhibitors that are (where applicable) modified to achieve i) modified spectrum of activity, organ specificity, and/or ii) improved potency, and/or iii) decreased toxicity (improved therapeutic index), and/or iv) decreased side effects, and/or v) modified onset of therapeutic action, duration of effect, and/or vi) modified pharmacokinetic parameters (resorption, distribution, metabolism and excretion), and/or vii) modified physico-chemical parameters (solubility, hygroscopicity, colour, taste, odour, stability, state), and/or viii) improved general specificity, organ/tissue specificity, and/or ix) optimized application form and route by (a) esterification of carboxyl groups, or (b) esterification of hydroxyl groups with carboxylic acids, or (c) esterification of hydroxyl groups to, e.g. phosphates, pyrophosphates or sulfates or hemi-succinates, or (d) formation of pharmaceutically acceptable salts, or (e) formation of pharmaceutically acceptable complexes, or (f) synthesis of pharmacologically active polymers, or (g) introduction of hydrophilic moieties, or (h) introduction/exchange of substituents on aromates or side chains, change of substituent pattern, or (i) modification by introduction of isosteric or bioisosteric moieties, or (j) synthesis of homologous compounds, or (k) introduction of branched side chains, or (k) conversion of alkyl substituents to cyclic analogues, or (l) derivatisation of hydroxyl groups to ketales, acetales, or (m) N-acetylation to amides, phenyl-carbamates, or (n) synthesis of Mannich bases, imines, or (o) transformation of ketones or aldehydes to Schiff's bases, oximes, acetales, ketales, enolesters, oxazolidines, thiazolidines; or combinations thereof.

The various steps recited above are generally known in the art. They include or rely on quantitative structure-action relationship (QSAR) analyses (Kubinyi, 1992), combinatorial biochemistry, classical chemistry and others (see, for example, Holzgrabe and Bechtold, 2000).

Preferably, the inhibitor is an siRNA or an shRNA.

In a preferred embodiment of the invention, the inhibitor reduces the number of or eliminates cancer stem cells (CSCs).

The term "cancer stem cells" as used herein refers to a cell population within the tumour that is resistant to treatment by chemotherapy or radiation, that has the ability to regenerate the tumour and/or that is characterised as cancer cells with a low proliferation rate. More preferably these CSCs are also characterized by the expression of CSC-markers. These markers may vary depending on the tumour. In the case of brain tumours and especially gliomas and glioblastomas, common markers include prominin, Sox2 and nestin, as well as other markers associated with neural stem cells. Additional markers associated with immature cells may also be expressed (Brunner et al., 2012; Magee et al., 2012; Venere et al., 2011).

As used herein, the term "reduces the number of cancer stem cells" indicates a lowering in the number of cancer stem cells, the mass of cancer stem cells and/or the degree of proliferation of cancer stem cells to less than 90%, more preferred less than 80%, less than 70%, less than 60% or less than 50% of the number or mass of CSCs before treatment. Yet more preferred are inhibitors lowering the number or the mass of CSCs to less than 25%, less than 10%, less than 5% or less than 1% of the numbers or the mass of CSCs before administration of the inhibitor.

The number of cancer stem cells may be determined, for example, by staining one or more CSC biomarkers and assessing the number of stained cells. This assessment can be performed e.g. by immunocytochemistry or FACS analysis. Methods for determining the presence of CSCs are well known in the art (see e.g. Singh et al., 2004). For example, cells from a biopsy can be dissociated and CSC markers expressed on or in these cells can be immune-labelled and analysed by microscopy or FACS. Alternatively, dissociated cells can be placed in culture to assess their CSC properties. Typically, the dissociated cells are placed in culture at an appropriate cell density and on a culture surface that does not allow attachment of the cells to the surface. Such surfaces are well known in the art. As a result of these culturing conditions, the cells form spheres, i.e. clusters of cells that are not attached to the plate. If a sphere contains CSCs then dissociating the sphere and re-plating of the cells should result in the formation of identical spheres.

The degree of proliferation can be assessed by staining for the proliferation marker Ki67, wherein a higher level of Ki67 expression is indicative of a higher degree of proliferation. Alternatively, the degree of proliferation can be assessed by incorporation of 5-bromo-2'-deoxyuridine (BrdU) or 5-ethynyl-2'-deoxyuridine (EdU). BrdU is a uridine derivative and a structural analog of thymidine, and can therefore be incorporated into DNA during the synthesis-phase of the cell cycle as a substitute for thymidine. Thus, it serves as a marker for proliferation. Protocols for assessing the degree of proliferation by incorporation of these agents are well known in the art and can be found, for example, in the world wide web (www) under de-de.invitrogen.com/site/de/de/home/References/protocols/cell-and-tissue-analysis/brdu-protocol/BrdU-Labeling-Protocol.html or under products.invitrogen.com/ivgn/product/A10044?ICID=%3Dsearch-product.

In accordance with the present invention, the term "eliminates cancer stem cells" relates to a reduction of the levels of CSCs to a level where no CSCs can be detected by the methods outlined above. Preferably, CSCs are considered to have been eliminated if no such cells can be detected by immunochemical detection of CSC-specific biomarkers such as, for example, prominin, Sox2, nestin or Hes3. As mentioned, no efficient treatment targeting cancer stem cells has been described to date. Since CSCs are resistant to established cancer therapies, the problem of tumour regeneration by the CSC and of subsequent relapses remains insufficiently addressed to date. Accordingly, the present invention provides inhibitors for the use in a novel, CSC-specific cancer therapy.

In a preferred embodiment of the present invention, the tumour to be treated is a brain tumour.

The term "brain tumour" describes the presence of an abnormal cell growth in the brain. This growth can originate in the brain and hence be a primary tumour or it can be a secondary tumour or metastasis in the brain. The secondary tumour in the brain can be derived from, for example, tumours of the lung, the breast, the kidney, the bladder, from germ cell tumours or from certain sarcomas or malignant melanoma. The brain tumours can, for example, be gliomas, meningiomas, pituitary adenomas, vestibular schwannomas, primary CNS lymphomas, and medulloblastomas. The term glioma includes, amongst others, astrocytomas, oligodendrogliomas, ependymomas, and choroid plexus papillomas.

Brain tumours, especially primary brain tumours, are often still associated with a poor prognosis and relapse after a first round of treatment is a relatively frequent event (Black, 1991). By targeting CSCs, the inhibitor used in accordance with the invention can address this issue. Thus, the use of inhibitors in accordance with the present invention for treating brain tumours is particularly useful.

In an alternative preferred embodiment of the present invention, the tumour to be treated is a pancreatic tumour. In another alternative preferred embodiment of the present invention, the tumour to be treated is a tumour of the eye. Tumours of the eye include, for example, retinoblastoma, rhabdomyosarcoma, intraocular lymphoma and intraocular melanoma.

In a preferred embodiment of the invention, the inhibitor is used in combination with a second therapeutic compound and/or radiation.

The second therapeutic compound can be selected from a group comprising proteins, peptides aptamers, siRNAs, shRNAs, miRNAs, ribozymes, antisense nucleic acid molecules, or small molecules. The selection is independent of the identity of the inhibitor used in accordance with the invention, i.e. the second therapeutic compound and the inhibitor may be selected from the same or different classes of compounds.

According to the present invention, the term "radiation" specifies ionizing radiation used as part of an anti-cancer treatment. The radiation may be delivered by external-beam radiation therapy (teletherapy), by internal, sealed source therapy (brachytherapy) or by systemic radiation therapy (unsealed source radiotherapy).

The term "ionizing radiation" is defined in accordance with the art and refers to the exposure to high-energy photons, as for example x-rays or gamma rays; or to electron or particle beams, including alpha particles, and beta particles; proton beams or neutron beams.

The combination of the inhibitor used in accordance with the present invention with a second therapeutic compound or with radiation is particularly useful because differentiated cancer cells are susceptible to radiation or a suitable second compound, whereas CSCs can be targeted by the inhibitor. The combination of the inhibitor used in accordance with the present invention with a second compound and/or radiation provides a further new aspect of an anti-cancer treatment having the advantage of targeting both differentiated tumour cells and CSCs.

In a more preferred embodiment, the second compound is a chemotherapeutic compound.

The term "chemotherapeutic compound" as used herein, describes compounds used to reduce the growth and/or survival of cancer cells. This includes, but is not limited to, substances impairing mitosis and substances inducing death of cancer cells by apoptosis, necrosis, necroptosis or any other form of cell death. More specifically, a chemotherapeutic compound can be, for example, an alkylating agent, an antimetabolite, an antibiotic, a plant alkaloid, a topoisomerase inhibitor, a kinase inhibitor or another anti-tumor agent. Although the term "chemotherapeutic compound" as used in the art does not typically comprise targeted therapies, these targeted therapeutics are comprised in the term in accordance with the present invention. Accordingly, the term chemotherapeutic compound also refers to compounds, such as for example monoclonal antibodies that interfere with specific targeted molecules needed for carcinogenesis and tumour growth. Such chemotherapeutic compounds are well known in the art and include for example bevacizumab, carmustine (BCNU), cis-platinum, cytarabine (Ara-C), cyclophosphamide (Cytoxan), doxorubicin (Adriamycin), erlotinib, etoposide (VP16), fluorouracil (5FU), gefitinib, gemcitabine, imatinib (Gleevec), mitotane (Lysodren), mitomycin C, oxaliplatin, paclitaxel (Taxol), temozolomide or vincristine. Further chemotherapeutics can also be used and are well known in the art, see e.g. the World-Wide-Web (www) at chemocare.com/chemotherapy/drug-info/default.aspx or at amspc.org/knowledge_objectives/druglist/chemotherapy.pdf. The selection of a suitable chemotherapeutic compound depends on a variety of factors such as the type and extent of the tumour and the age and general health of the subject. A suitable compound as well as its dosage will therefore be determined by the attending physician.

Further, the present invention relates to an in-vitro method for diagnosing a tumour, comprising determining the amount of Hes3 protein in cerebrospinal fluid (CSF)-derived samples obtained from a subject, wherein an increased amount of Hes3 protein is indicative of the presence of a tumour.

The term "in-vitro method" as used according with the present invention refers to processes determining the amount of Hes3 in a sample in a setting outside a living being. Although the sample may be obtained from a living being, such as a mammal or preferably a human, the step of obtaining the sample is not considered to be comprised in the method according to the present invention.

Concerning the term "tumour" the definition provided elsewhere herein applies mutatis mutandis also to this case. Preferably, tumour is a primary brain tumour. More preferably the tumour is a meningioma I or glioblastoma multiforme grade IV.

The term "determining the amount" as used in accordance with the present invention refers to determining not only the presence or absence of a protein but also its (precise) absolute or relative amounts. Methods for the determination of the amount of Hes3 in a sample derived from a bodily fluid include, without being limiting, western blotting, dot blotting, ELISA; FACS and mass spectrometry. The term "relative amount" as used herein refers to the amount of a given sample in comparison to a normal value. In accordance with the present invention the term "normal value" refers to the amount of Hes3 protein in a CSF-derived sample obtained from a subject that does not have a tumour. Preferably, the subject is "healthy", i.e. is unknown to be afflicted with a disease. It will be appreciated by the skilled person that determining this normal value may be carried out prior to performing the present method of the invention, such that the determined value may be used as a reference at later times whenever a sample is analysed in accordance with the method of the present invention; or may be determined in parallel each time a sample is analysed in accordance with the method of the present invention. The normal value may also be determined only once and stored as a standard for all future tests.

Alternatively, the normal value may be determined in parallel each time a sample is analysed in accordance with the method of the present invention. Whether a subject has a tumour can be established, for example, by reviewing the medical history, conducting a physical and/or a neurological examination and by applying suitable imaging tests such as, for example, MRI, CT-scan or PET scan. Preferably, the subject not having a tumour is matched to the subject whose CSF-derived sample is to be analysed in age, gender and/or ethnic background. Instead of as a normal value, the standard amount of Hes3 present in CSF-derived samples obtained from subjects not having a tumour may also be represented as a standard range of values, which may be referred to as "normal range". Consequently, the relative amount of Hes3 in a given sample may also be established by comparison to this "normal range".

The term "absolute amount" as used herein refers to an amount that is given without reference to another value. Preferably, the absolute amount can be represented in units commonly used to represent concentrations such as mg/L, µg/mL, nmol/L etc.

The term "increased amount" refers to a statistically significant increase of Hes3 as compared to the normal value or normal range as defined above. It will be appreciated in this regard that the threshold value above which the amount of Hes3 is indicative of a tumour may vary slightly depending on the population of patients investigated as well as on the investigative method. Thus, it may be necessary to establish individual borderline values by the use of procedures and/or reagents suitable to standardise measurements. The skilled person knows how to establish such borderline or threshold values. For example, the expression levels of Hes3 could be measured by the method of interest simultaneously in at least 10, more preferably at least 75 and most preferably at least 100 patients and statistical methods could be employed to establish the borderline value for the individual method.

Preferably, an amount of Hes3 that is increased to at least 1.5-fold the normal value.

The term "at least", as used herein, refers to the specifically recited amount but also to more than the specifically recited amount or number. For example, the term "at least 1.5 fold" encompasses also at least 2-fold, at least 2.5-fold, at least 3-fold, at least 3.5-fold, at least 4-fold, at least 4.5-fold, at least 5-fold, at least 5.5-fold, at least 6-fold, at least 6.5-fold, at least 7-fold, at least 7.5-fold, such as at least 8-fold, at least 8.5-fold, at least 9-fold at least 9.5-fold at least 10-fold and so on. Furthermore, this term also encompasses exactly 1.5-fold, exactly 2-fold, exactly 2.5-fold, exactly 3-fold, exactly 3.5-fold, exactly 4-fold, exactly 4.5-fold, exactly 5-fold, exactly 5.5-fold, exactly 6-fold, exactly 6.5-fold, exactly 7-fold, exactly 7.5-fold, exactly 8-fold, exactly 8.5-fold, exactly 9-fold, exactly 10-fold and so on.

More preferably, the amount of Hes3 is increased to at least 4-fold the normal value.

In accordance with the present invention the term "CSF-derived samples" refers to samples obtained from spinal taps of a patient which have been processed to meet the requirements of the respective analysis method. Optionally, the sample may be frozen for storage at −80° C. before processing. Appropriate steps for processing a sample are well known in the art and may include addition of reagents such as, for example, Laemmli buffer or (labelled) antibodies, and/or the incubation at a specified temperature, such as for example boiling of a sample.

The definition of the term "subject" as provided elsewhere in this case applies mutatis mutandis also for this embodiment.

To date the diagnosis of tumours often relies on the analysis of patient biopsies. However, obtaining a biopsy requires a highly invasive procedure. In addition, the histopathological analysis and classification of biopsies can be unsatisfactory due to a lack in reproducibility. Alternatively, the presence of biomarkers in bodily fluids can be assessed. Bodily fluids such as e.g. blood, urine, pleural fluid, and cerebrospinal fluid (CSF) represent a good source for disease markers because they are readily accessible, in a process that is less invasive than obtaining a biopsy, and represent drainage products from involved tissues. The contents of these fluids can be assessed by quantitative methods. Therefore, diagnostic, prognostic and predictive methods, based on the analysis of biomarkers in bodily fluids, are not only less invasive but also provide a better, more reproducible way of quantification and classification.

Depending on the type of tumour, different bodily fluids are relevant for the analysis. In case of brain tumours, biomarkers can often be identified in plasma, serum, or in CSF-derived samples. The analysis of blood-derived samples has the disadvantages that the concentration of the relevant biomarker can be very low in comparison to abundant proteins such as immunoglobulins and albumin, that biomarkers derived from the central nervous system (CNS) can be very diluted in the peripheral circulation or not even get there due to the blood-brain barrier, and that the detection of a biomarker in the blood does not always allow conclusions regarding its source, i.e. the tissue it is derived from.

For this reason, CSF can be a better source for samples for the detection of biomarkers. CSF is a clear largely cell-free fluid composed of water, glucose, salts, metabolites, nucleic acids, peptides and proteins, wherein the overall protein content is at least an order of magnitude lower than in serum. It circulates within the ventricles, the spinal column, and around the brain in a cavity referred to as sub-arachnoid space. The protein profile of CSF therefore originates mainly from the CNS. Consequently, CSF is a valuable source of samples to be employed in diagnostic, prognostic and predictive methods regarding brain malignancies. A further advantage is that the composition of normal human CSF has been established and that a reference is therefore available (Kalinina et al., 2011).

A number of biomarkers indicative of the presence of tumours have been identified, of which some can be detected in bodily fluids such as CSF. However, none of these markers provides conclusive evidence regarding the presence of CSCs.

Surprisingly, Hes3 can be detected in CSF-derived samples obtained from a subject. This is unexpected because Hes3 is a transcription factor and this class of proteins is not typically secreted but rather has a cytoplasmic or nuclear localisation. Based on this surprising discovery, detecting Hes3 in a CSF-derived sample can be employed in determining the presence or absence of CSCs in the brain, i.e. an increased amount of Hes3 as compared to the normal value as defined above indicates the presence of CSCs. The presence of CSCs is in turn indicative of the presence of a tumour and more specifically of an aggressive tumour. Thus, the present invention provides an in-vitro method for detecting the presence of cancer stem cells (CSCs) by determining the level of Hes3 in a cerebrospinal fluid-derived sample.

Further the invention also provides an in-vitro method of diagnosing a tumour by determining the level of Hes3 in a CSF-derived sample. The latter in-vitro method for diagnosis of a tumour of the present invention not only provides an alternative method but also represents an improvement because it overcomes the disadvantage that the presence of CSCs cannot be detected which is common with the detection of other markers in bodily fluids.

In a preferred embodiment of the method of the invention, the presence and/or amount of Hes3 in a CSF-derived sample is/are detected using an antibody and/or mass spectrometry.

The term "detected using an antibody" as used herein refers to any detection method making use of the recognition of Hes3 by a Hes3-specific antibody. These methods include, but are not limited to, western blotting, ELISA, and intracellular FACS analysis. Generally, these methods and their use for the quantification of proteins are well known in the art.

The term "mass spectrometry" is defined in accordance with the art and refers to an analytical technique in which the components of a sample are ionized and identified by the mass-to-charge ration of these charged molecules and/or molecule fragments. These methods as well as its quantitative variants are well known in the art and are described e.g. in Petriz et al., 2011 or in Paolo et al., 2012.

In another preferred embodiment of the method of the invention, the amount of Hes3 protein positively correlates with the aggressiveness of the tumour.

The term "correlates with the aggressiveness of the tumour" as used herein describes the existence of a direct relation between the level of Hes3 protein and the aggressiveness of the tumour. Higher levels of Hes3 positively correlate with the aggressiveness of the tumour and therefore are indicative of the tumour being more aggressive than a tumour being associated with lower levels of Hes3.

In accordance with the present invention the term "aggressiveness" relates to the tendency of a tumour to grow fast, spread quickly and to invade other tissues. In the art, the aggressiveness of a tumour is often expressed in terms of its grade. The most commonly used system for grading tumours is the system according to the guidelines of the American Joint Commission on Cancer. As per these guidelines, the following grading categories are distinguished: GX (grade cannot be assessed), G1 (well-differentiated; low grade), G2 (moderately differentiated; intermediate grade), G3 (poorly differentiated, high grade); G4 (undifferentiated, high grade). The higher the grade of a tumour the more aggressive it is considered to be (Louis et al., 2007). Thus, the determination of the amount of Hes3 in CSF-derived samples may be used, potentially in combination with other techniques, in the process of grading a tumour.

The additional information concerning not only the presence of a tumour but also its aggressiveness can be employed to establish a prognosis and to select and/or adjust treatment of the tumour accordingly.

In a preferred embodiment, the CSF-derived samples are obtained from a human.

In another preferred embodiment, the tumour is a brain tumour.

As mentioned previously herein, brain tumours, especially primary brain tumours, are often still associated with a poor prognosis (Black, 1991). Depending on extent and aggressiveness these tumours are targeted by different treatment options. The application of the method for diagnosing a tumour and assessing its aggressiveness to a brain tumour is therefore particularly useful as it may assist in selecting the most appropriate treatment option and in improving the prognosis.

The figures show:

FIG. 1. Therapeutic Potential of Targeting Hes3.

Tumours contain several populations of cells which differ in their potential to regenerate the tumour. Current therapies are efficient at targeting some populations and thus reduce tumour size. However, the cancer stem cell (CSC) population, which is responsible for regenerating the tumour, is not efficiently targeted. Therefore current therapies are not efficient at inhibiting relapse and metastasis. However, CSCs can be targeted by manipulating Hes3. Inhibitors of Hes3 are therefore useful in a novel strategy of CSC-specific anti-cancer medicine.

Figure 2:
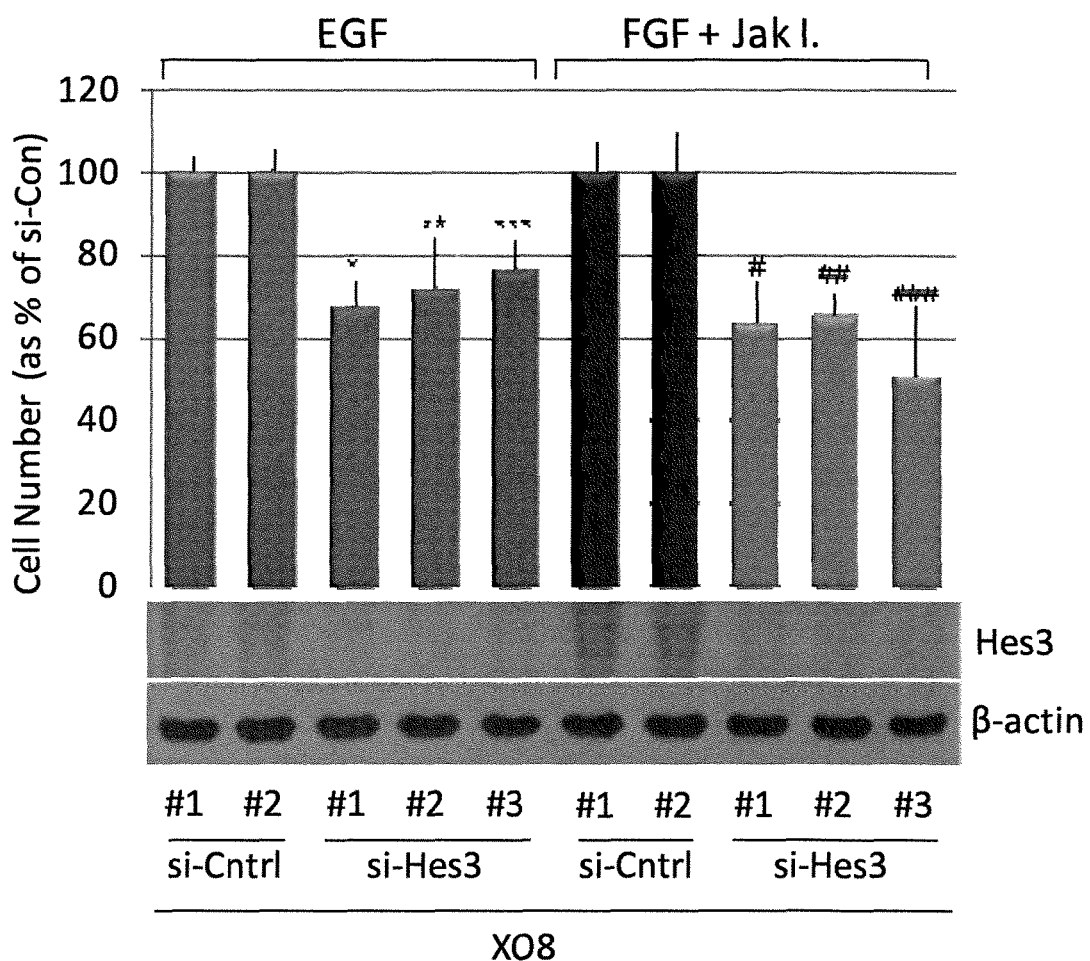

FIG. 2. Cell Numbers of XO-8 Cultures in Presence or Absence of Hes3 Knockdown.

The bars show the numbers of XO-8 cells, cultured with EGF or bFGF+JAK kinase inhibitor as indicated above the bars, in case of Hes3 knockdown (each of the bars represent the use of a different siRNA-siHes3 #1 to #3) as % of the control (si-cntrl #1 and #2). The knockdown efficacy as assessed by western blotting is shown underneath. The labelling to the right (Hes3 and β-actin) indicates the antibodies used to probe the western blotting membranes.

Figure 3:
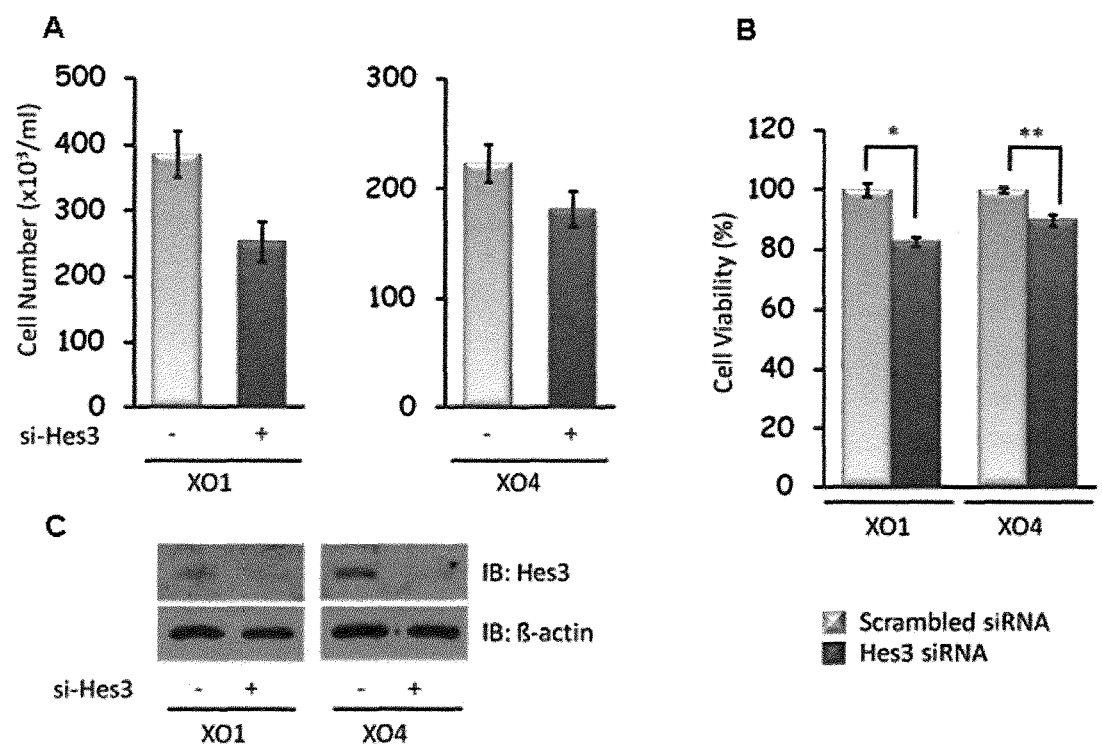

FIG. 3. Cell Numbers and Cell Viability of XO-1 and XO-4 Cells in Presence or Absence of Hes3 Knockdown.

Panels A and B. Differences between control (light grey bars) and Hes3 knockdown conditions (dark grey bars) in XO-1 (left part of each panel) and XO-4 cells (right part of each panel) in cell numbers (A) and in cell viability as assessed by MTS viability assay (Promega) and represented as % of control (B), are shown. * and ** indicate statistical significance of the differences. Panel C shows the protein levels of Hes3 in XO-1 (left) and XO-4 (right) cells in absence (−) or presence (+) of transfection with a Hes3 siRNA as assessed by western blotting. The antibodies used for immunoblotting are indicated to the right (IB: Hes3 and IB: β-actin).

Figure 4:
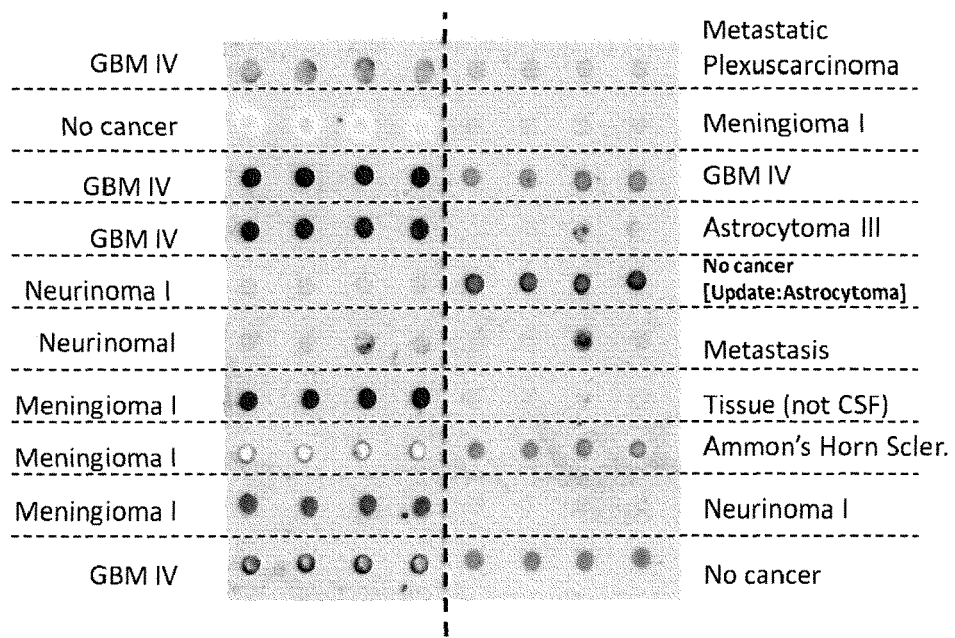

FIG. 4. Hes3 as a Biomarker for Brain Tumours.

The level of Hes3 in CSF-derived samples of patients or subjections without a cancer diagnosis was assessed in quadruplicates by dot blotting. The labelling to the left and right of the blot indicates the respective diagnosis. In one case the original diagnosis of "no cancer" was later updated to astrocytoma. The updated diagnosis is shown in square brackets in the Figure. Samples were applied to nitrocellulose paper and Hes3 was detected by an anti-Hes3 antibody and subsequent visualization and chemiluminescence detection.

Figure 5:
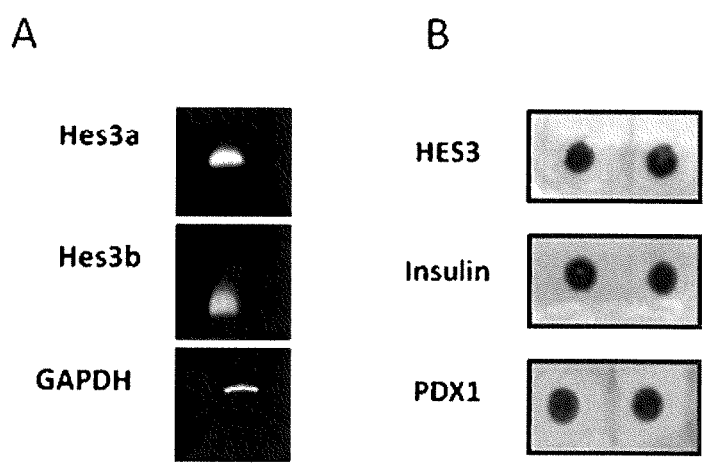

FIG. 5. Hes3 is Expressed in Pancreas

A: Reverse-transcriptase PCR shows that both transcripts of Hes3 (Hes3a and Hes3b) are expressed in the adult mouse pancreas. GAPDH was used as a house keeping gene. B: Dot blot showing that Hes3 protein is expressed in the adult human pancreas.

Figure 6:
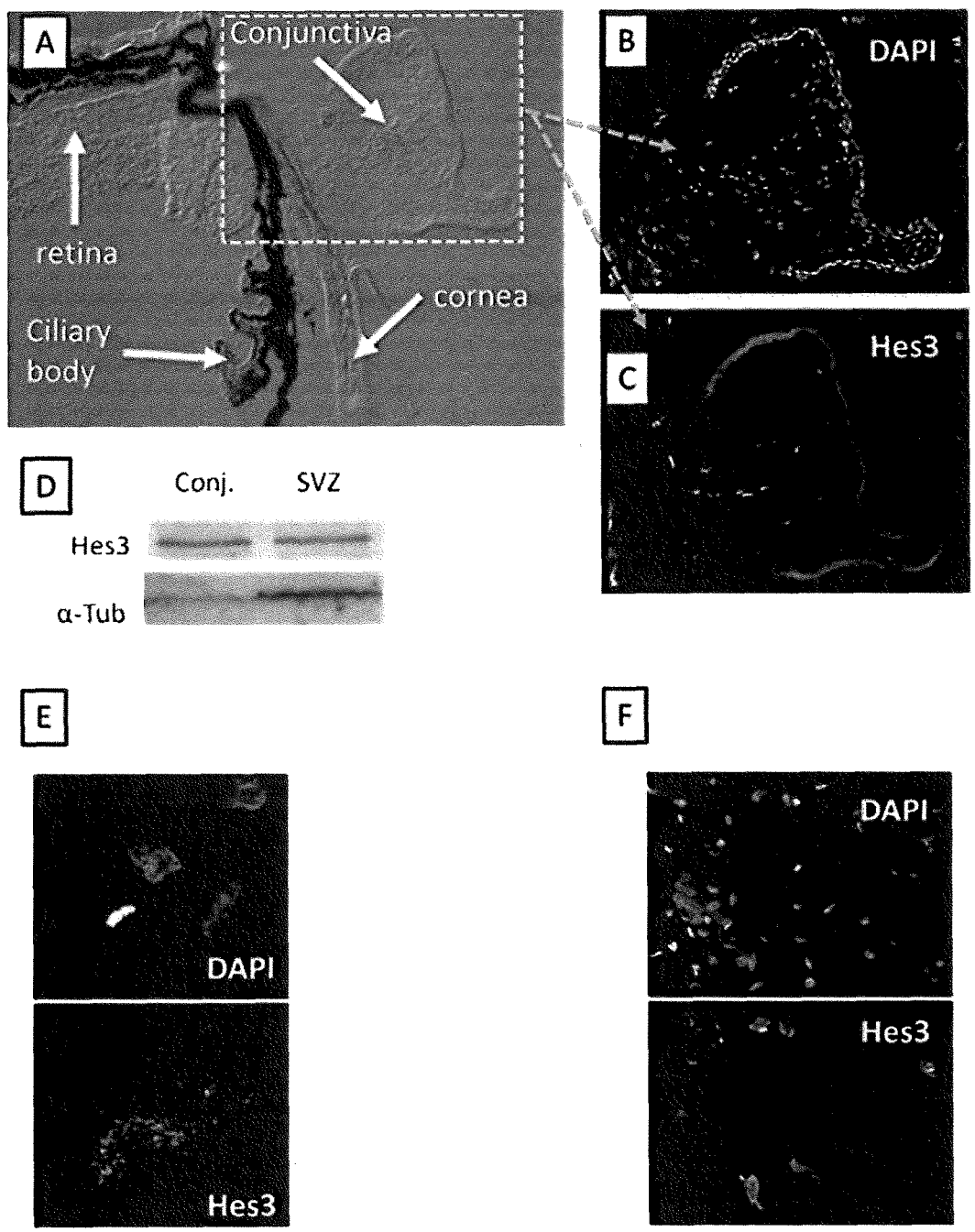

FIG. 6. Hes3 is Expressed in the Eye and in Pterygium.

A: Image of a dissected adult mouse eye; key identifying anatomical features are marked with arrows. B, C: Immunohistochemical detection of Hes3 in the conjunctiva of the adult mouse eye. Nuclei are stained with DAPI. D: Western blotting for Hes3 in a dissected mouse conjunctiva (Conj.) shows the presence of Hes3; as a positive control, tissue from an adult mouse subventricular zone (SVZ; an area of the brain) was used. E: Immunohistochemical detection of Hes3 in the adult human eye. The limbus was used for staining and nuclei are stained with DAPI. The image was acquired at high-magnification and shows a single Hes3+ cell. F Immunohistochemical detection of Hes3 in the adult human pterygium. Nuclei are stained with DAPI.

Figure 7:
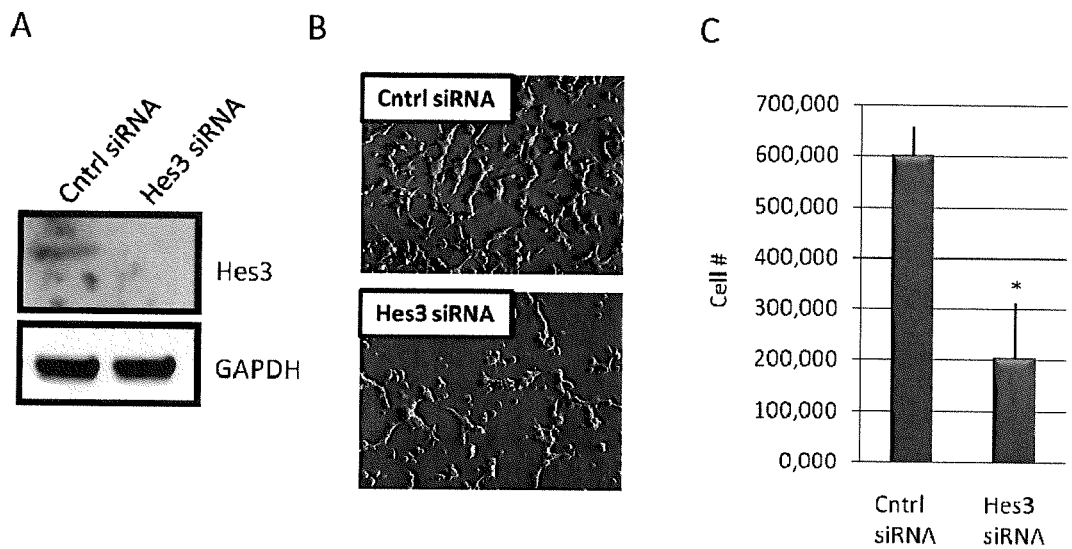
Figure 7:
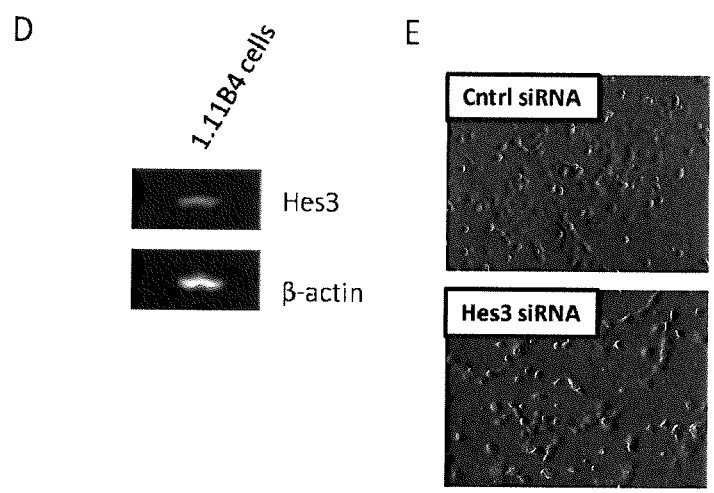

FIG. 7. Hes3 siRNA Interference Opposes the Growth of Two Pancreatic Cell Lines in Culture.

(A) MIN6 cells cultured under serum-free conditions express Hes3. The protein levels of Hes3 two days after transfection with a control (scrambled, "Cntrl siRNA") or an siRNA against Hes3 as assessed by western blotting are shown. As expected, Hes3 is expressed following transfection of cells with a control siRNA whereas after transfection with an siRNA against Hes3, expression of Hes3 is markedly reduced. Antibodies used for immunoblotting are indicated to the right. GAPDH was used to demonstrate that an equal amount of cell extract was loaded into the Western blotting gel for both samples. (B) Transfection of MIN6 cells with Hes3 siRNA reduces the number of cells compared with transfection using a control siRNA. Representative brightfield images are shown. (C) Transfection of MIN6 cells with a Hes3 siRNA reduces cell number relative to transfection with using a control siRNA; the graph shows cell number per field of view as determined by counts on images of cells stained with the nuclear dye DAPI. (D) 1.1B4 cells in culture express Hes3. Data are from reverse transcriptase PCR using a primer set for Hes3. Beta-actin was used as the housekeeping gene. (E) Transfection of MIN6 cells with Hes3 siRNA reduces the number of cells compared with transfection using a control siRNA. Representative brightfield images are shown.

Figure 8:
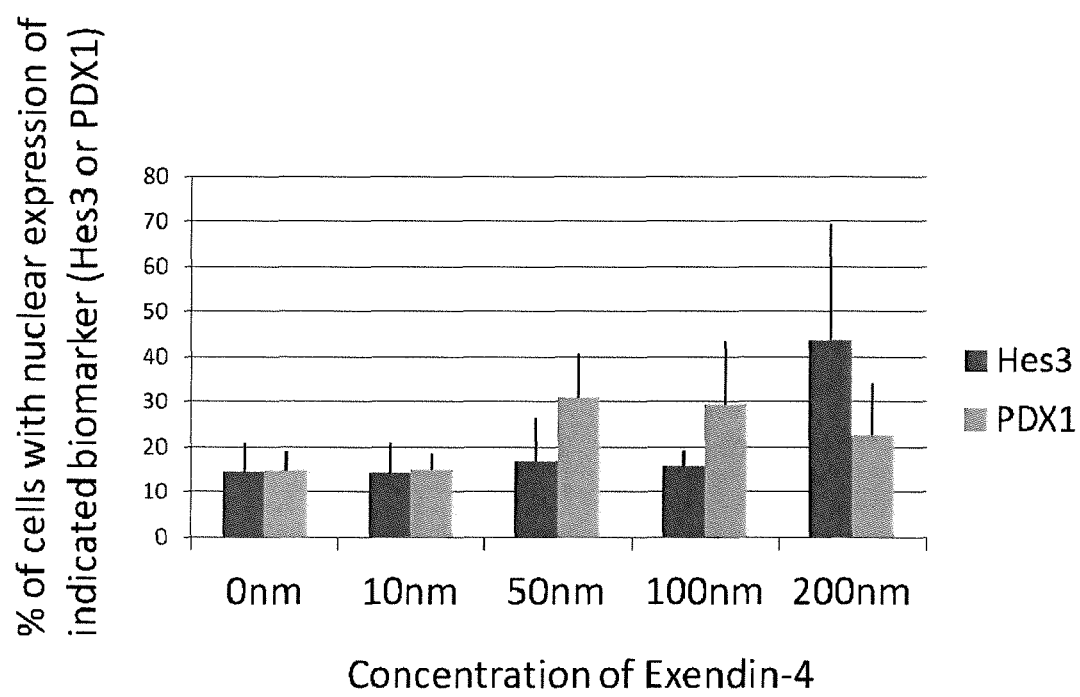

FIG. 8. The Expression of Hes3 can be Modulated.

Graph showing the percentage of cultured MIN6 cells exhibiting nuclear expression of Hes3 or PDX1 as determined by fluorescence microscopy after treatment with the indicated concentrations of Exendin-4.

The examples illustrate the invention:

EXAMPLE 1

Material and Methods

Culturing of XO Cell Lines

Three GBM cell lines ("X01", "X04", and "X08" lines) were established from acutely resected human tumor tissues (Glioblastoma multiforme). Tissue was dissected under a dissection microscope, triturated in 1 ml N2 medium containing bFGF with a 1 ml pipette until no tissue clumps were seen; the triturate was allowed to settle for 1 min and the top 0.9 ml was collected, diluted in N2 containing bFGF and plated. Cells were expanded in serum-free DMEM/F12 medium with N2 supplement and bFGF (20 ng/ml) for 5 days under 5% oxygen conditions (i.e. under conditions promoting the expression of Hes3 and the survival and maintenance of CSCs) and were re-plated fresh or from frozen stocks at 1,000-10,000 cells per $cm^2$. bFGF was included throughout our experiments, unless otherwise stated.

Pharmacological Treatments.

bFGF and EGF were purchased from RnD Systems and were used at a concentration of 20 ng/ml. JAK inhibitor was purchased from Calbiochem and was used at a concentration of 200 nM.

Electroporation of siRNA

We used the Amaxa nucleofector equipment to electroporate siRNA into GBM cell cultures. Two control siRNA products were used (Santa Cruz Biotechnology, sc37007 and OriGene Tech, SR3004) and three anti-Hes3 siRNA products (Santa Cruz Biotechnology, sc88003 and OriGene Tech, SR318208A and SR318208C). The day before transfection, 5 million cells were dissociated from a culture flask and transferred to T25 Falcon culture flask with suspension medium containing EGF or bFGF. Cells were then transfected with siRNA using a nucleofecting electroporator according to the manufacturer's protocol (Amaxa Inc., Gaithersburg, Md., USA). After 24 h, the medium was replaced, and cells were harvested for additional experiments. Typical transfection efficiency was at approximately 80%.

Assessment of Cell Numbers

Monolayer cultures were used for these experiments. 5 representative images were taken from each culture well. To ensure reproducibility, the 5 pictures were taken as follows: The first picture was from the centre of the well and four others were taken above, below, left, and right of the centre of the well, forming a cross. Images were taken using brightfield and fluorescent acquisitions. For the fluorescent acquisition, cells were stained with DAPI which labels nuclei. Images were exported to an image analysis program and cell number was counted manually. The combination of stained nuclei and brightfield images ensured that only living cells were counted.

Western Blotting and Dot Blotting.

Western Blot analyses were performed using standard protocols. Briefly, Laemmli Sample Buffer from Bio-Rad was used as the harvesting buffer. Samples were boiled for 15 min and approximately 40 microgram of protein was loaded per well. Primary antibodies were used at a dilution of 1:500 and secondary antibodies at 1:4,000. Antibodies were diluted in 5% BSA in PBST. Primary antibodies were incubated overnight, with mild shaking, at 4 degrees Celsius. The following antibodies were employed: Hes3 antibody #25393 from Santa Cruz, β-actin antibody (Santa Cruz Biotechnologies, sc-47778) and GAPDH antibody from R&D Systems (cat. # AF5718).

Viability Analysis

Cell viability was measured by the MTS assay (Promega).

Statistical Analysis

Results shown are the mean±S.D. Asterisks identify experimental groups that were significantly different (p-value<0.05) from control groups by the Student's t-test (Microsoft Excel), where applicable.

Transfection of MIN6 and 1.1.B4 Cells with siRNA

Transfections were performed using the lipofectamine 2000 reagent in accordance with the manufacturer's instructions. Commercially available control and Hes3 siRNA products were used. Assays (determination of cell number, western blotting, PCR, imaging) were performed 2 days after transfection onset. For transfection of 1.1.B4 cells the same siRNAs were used as for the electroporation of GBM cell lines. For MIN6 cells a Hes3 siRNA from Santa Cruz Biotechnology (cat. # sc-37942) and a control ("scrambled") siRNA also from Santa Cruz Biotechnology (sc-37007) were used.

PCR

Reverse transcriptase PCR was performed using a standard procedure described for example in Park et al., 2013. A primer set for Hes3 and a primer set for the house-keeping gene beta-actin (β-actin) was used.

Cell Culture of MIN6 Cells

MIN6 cells (mouse insulinoma cells; commercially available, for example, from AddexBio, Catalog #: C0018008)) were grown in either serum containing medium (DMEM (Life Technologies, 61965-026), 15% Fetal Calf Serum (Biochrom Superior, F0615), 70 µM 2-Mercaptoethanol (Sigma Aldrich, M6250), 100 µg/mL Pen-Strep (Life Technologies, 15140-122)) or serum free N2 medium (DMEM-F12 (Sigma Aldrich, D8062), 100 µg/mL Apo-Transferrin (Sigma Aldrich, T2036), 20 nM Progesterone (Sigma Aldrich, P8783), 100 µM Putrescine (Sigma Aldrich, P5780), 30 nM Selenite (Sigma Aldrich, S5261), 100 µg/mL Pen-Strep)). To examine changes in the properties of MIN6 under different culture conditions, cells were first maintained in serum containing medium for 5 days. Cells were then passaged and grown under serum free conditions for another 5 days. The cells were then passaged again, back into serum containing medium ("Return") for an additional 5 days prior to analysis. Serum and no serum controls were run in parallel in which the cells were maintained in either serum containing or serum free conditions for the final 10 days of the experiment.

Exendin-4 Treatment

Cells were seeded at 50,000 cells per 24 well-plate and treated with different concentrations of Exendin-4 (0 nM, 10 nM, 50 nM, 100 nM, and 200 nM). Exendin-4 was purchased from Biotrend (catalog number: BP0111). Exendin-4 was added to the culture medium beginning at 24 hours after plating. Exendin-4 was added every two days during medium changes, and cells were fixed and immunostained at day 5.

RNA Isolation and Reverse Transcriptase PCR

RNA was extracted from whole pancreas or MIN6 cells using High Pure RNA isolation kit (Roche, 11828665001) and reverse transcribed using Promega M-MLV reverse transcriptase (Promega, M170B). PCR was performed for HES3a, HES3b, PDX1, Insulin and GAPDH (primers described in supplemental materials and methods) using Dream Taq Green DNA polymerase (Thermo Scientific, EP0711).

Western Blot

MIN6 cells were grown in 6-well plates for 5 days, then lysed with 500 µl CytoBuster Protein Extraction Reagent (Novagen, 71009-3) contain protease inhibitors (Sigma Aldrich, P8340). Samples were resolved by western blot using standard techniques.

Immunohistochemistry/Immunocytochemistry

Pancreata were fixed by transcardial perfusion with 4% PFA followed by post-fixation overnight at 4° C. The tissue was cryoprotected with 30% sucrose and embedded in OCT compound (Sakura, 4583). 12-14 µm sections were cut and mounted on glass slides. MIN6 cells were fixed in 4% PFA for 30 min. Both the sections and cells were permeabilized in 0.1% Triton X-100 in PBS and blocked in 5% powdered milk and 0.1% Triton X-100 in PBS prior to incubation with primary antibody (see supplemental materials and methods for antibodies and dilutions). Images were taken using a laser confocal microscope (LEICA, Germany).

Tissue Sourcing

Adult C57BL/6 mice (post-natal day 29) were used for tissue sourcing. Under deep anesthesia, animals were perfused transcardially with a rinse of saline, followed by 4% paraformaldehyde fixative (pH 7.4). Tissues were removed immediately, stored in the fixative solution overnight, and then in 30% sucrose for 2 days. Tissues were frozensectioned at 16 or 30 micrometers. Immunohistochemistry was performed using standard procedures (8). For Western blotting analysis, tissues were dissected, protein extracts were prepared and separated under reducing conditions. Animals were handled and housed according to the German Federal guidelines for the use and care of laboratory animals and the study was approved by the Landesdirektion Dresden.

Hes3 Positive Cell Quantification

For the quantification of Hes3+ cells in tissues, several mice were used (N=5-10); from each mouse 6 or more anatomically matched sections were used for counting.

Human Samples

The pterygium samples (samples from 10 patients were examined) were collected by standard pterygium surgery. The surgery was performed when the patient complained about discomfort, visual impairment, induction of astigmatism or documented pterygium progression. Briefly, the eye was anesthesized, the pterygium head was mobilised from the cornea and the body was separated from the healthy conjunctiva. Finally the conjunctiva was sutured. (Protocol# EK 87032012)

Reagents Used in Investigating the Expression of Hes3 in the Eye

The primary antibodies used in analysing Hes3 expression in the eye were against: Hes3 (Santa Cruz Biotechnology, sc-25393), CD31 (Invitrogen, 37-0700), pan-p63 (Santa Cruz Biotechnology, sc-8431), K13 (Progen Biotechnik, 61007). Secondary antibodies were from Molecular Probes. General reagents were from Sigma-Aldrich.

EXAMPLE 2

Knockdown of Hes3 Reduces Cell Numbers of the Primary Human Glioblastoma Multiforme Cell Line XO-8

To address whether the expression of Hes3 contributes to cell growth, siRNA interference with CSC cultures in the presence of EGF or bFGF+JAK kinase inhibitor (i.e. conditions which support Hes3 expression) was performed. Two control ("scrambled") siRNAs and three siRNA species against Hes3 were used. All three showed significant reduction in cell number, 5 days after electroporation. Reduction of Hes3 protein was assessed by Western blotting. This reduction shows that Hes3 is required for survival and maintenance of CSCs and is thus predictive of the therapeutic potential of compounds reducing the expression or activity of Hes3.

EXAMPLE 3

Knockdown of Hes3 Reduces Cell Numbers and Viability of the Primary Human Glioblastoma Multiforme Cell Lines XO-1 and XO-4

To corroborate the data obtained in example 2, knockdown of Hes3 was performed in two additional glioblastoma CSC cell lines (XO-1 and XO-4). Following electroporation to introduce the siRNAs, the cells were cultured in EGF-containing medium for 5 days. Subsequently, cell numbers were determined and cell viability was estimated by a cell viability assay (Promega MTS). Again, Hes3 siRNA reduced the cell numbers as well as the cell viability as compared to control siRNA. These results show that cancer stem cells depend on Hes3 for survival and maintenance and that Hes3 is a novel therapeutic target that specifically attacks the elusive cancer stem cell population.

EXAMPLE 4

The Levels of Hes3 Protein Detectable in CSF-derived Samples Correlate Positively with the Presence of Aggressive Brain Tumours CSF samples were collected from the neurosurgery department as frozen samples (stored at −80° C.). Samples were processed by boiling in the presence of laemmli buffer for 10 min. 2 microliters of each sample were loaded onto nitrocellulose paper (in quadruplicates to demonstrate reproducibility). The samples were allowed to dry on the paper before Hes3 was detected using a specific anti-Hes3 antibody. The relative amount of Hes3 was determined by densitometry followed by the calculation of fold differences between samples derived from patients with tumours and samples derived from subjects without a cancer diagnosis.

Using this technique it was determined that the most aggressive tumours show a greater amount of Hes3 in their CSF than the less aggressive tumours. In contrast, CSF from control (no tumour) patients exhibited non-detectable levels. In one example, the fold-difference between CSF from a patient with no cancer diagnosis and a patient with glioblastoma multiforme grade IV was 11.9.

In the original CSF samples tested, CSF samples from three patients without cancer diagnosis were included ("No cancer"). The measurements showed elevated Hes3 in one of these "control" samples. We then contacted the medics who followed the patients and they informed us that in the weeks/months since the initial cancer-free diagnosis, the official diagnosis of the patient with the high levels of Hes3 had been changed to astrocytoma. In other words, in this example, the method predicted cancer before the medical evaluation.

The results obtained for the different tumours are shown in FIG. 4 and summarized in table 1.

TABLE 1

| Sample # | Diagnosis | Level of Hes3 (undetectable, low, medium, high) |
|---|---|---|
| 1 | No cancer diagnosis (control) | undetectable |
| 2 | No cancer diagnosis (control) | Undetectable |
| 3 | No cancer diagnosis (control) | Undetectable |
| 4 | No cancer diagnosis (control) | Undetectable |
| 5 | No cancer diagnosis (control) | Undetectable |
| 6 | No cancer diagnosis (control) | Undetectable |
| 7 | No cancer diagnosis (control) | Undetectable |
| 8 | No cancer diagnosis (control) | Undetectable |
| 9 | No cancer diagnosis (control) | Undetectable |
| 10 | Neurinoma I | Undetectable |
| 11 | Neurinoma I | Undetectable |
| 12 | Neurinoma I | Undetectable |
| 13 | Metastatic plexus carinoma | Low |
| 14 | Astrocytoma | Low |
| 15 | Meningioma I | Low |
| 16 | Meningioma I | Low |

TABLE 1-continued

| Sample # | Diagnosis | Level of Hes3 (undetectable, low, medium, high) |
|---|---|---|
| 17 | Meningioma I | High |
| 18 | Meningioma I | High |
| 19 | Glioblastoma Multiforme Grade IV | Medium |
| 20 | Glioblastoma Multiforme Grade IV | Medium |
| 21 | Glioblastoma Multiforme Grade IV | High |
| 22 | Glioblastoma Multiforme Grade IV | High |
| 23 | Glioblastoma Multiforme Grade IV | High |

EXAMPLE 5

Hes3 is Expressed in Different Tissues

Tumours arising from Hes3-expressing tissues are promising targets for a treatment with Hes3 inhibitors. To investigate other tissues for the expression of Hes3, adult mouse (FIG. 5A) and human pancreas (FIG. 5B) was analysed for the expression of Hes3. The mRNA for both isoforms of Hes3 was detected in samples derived from adult mouse pancreas by PCR (FIG. 5A) and Hes3 was also shown to be expressed in human adult pancreas. Further, expression was also detected in the adult mouse eye (FIG. 6A to D), in the adult human eye (FIG. 6E) and in human ptergyium, a benign growth of the conjunctiva (FIG. 6F). These results show that Hes3 is expressed not only in the brain but also in other tissues such as the pancreas and the eye. It has previously been reported that mice in which Hes3 has been genetically deleted show no overt phenotype (Androutsellis-Theotokis et al., (2008) Cold Spring Herb Symp Quant Biol 73, 403-10; Hirata, et al., (2001) Embo J 20, 4454-66. This indicates that Hes3 is not essential for the survival of normal cells. On the other hand, CSCs and cancer cells acting as CSCs have been shown herein to depend on Hes3 for survival (FIGS. 3 and 7). This shows that cancer cells are susceptible to the inhibition of Hes3 while treatment with an Hes3 inhibitor does not appear to affect normal cells. Accordingly, inhibition of Hes3 is not only an option for brain tumours but also for tumours arising from other Hes3-expressing tissues.

EXAMPLE 6

Hes3 siRNA Interference Opposes the Growth of Two Pancreatic Cell Lines in Culture To further show that the effect on cell numbers induced by knockdown of Hes3 was not specific to glioblastoma CSC cell lines but that cells from a different tissue origin were similarly affected, knockdown of Hes3 was performed in two cancerous pancreatic cell lines, MIN6 and 1.1B4. MIN6 cells are a mouse insulinoma cell line derived from transgenic mice expressing the large T-antigen of SV40 in pancreatic beta cells. 1.1B4 cells are a hybrid cell line, derived from the fusion of human ductal cell carcinoma cells and human pancreatic beta cells. They can be used to model pancreatic ductal epithelial cancer. Although not generally considered to be cancer stem cells (CSCs), under the cell culture conditions employed these cells operate as CSCs, i.e. they utilise signal transduction pathways typical of CSCs.

This is shown by the expression of the CSC marker Hes3 (FIGS. 7 A and D). Following transfection with siRNAs, the cells were cultured for 2 days. Subsequently, cell numbers were determined. As in the glioblastoma cell lines, Hes3 siRNA reduced the cell numbers as compared to control siRNA also in the pancreatic cell lines (FIGS. 7 B, C and E). These results show that not only glioblastoma multiforme cells but also other CSCs or cancer cells operating as CSCs from other tissues require Hes3 for survival.

EXAMPLE 7

Hes3 Expression can be Modulated

To identify further means of regulating Hes3 function, Exendin-4 was tested for its ability to influence Hes3 nuclear localisation. For this purpose, cultured MIN6 cells were treated with different concentrations of Exendin-4 as described in Example 1 herein above. At the end of the treatment period, cells were fixed with 4% paraformaldehyde and immune-labeled for Hes3 and PDX-1. Then, using fluorescence microscopy, images were acquired and analyzed to determine the percentage of cells that express Hes3 in the nucleus and the percentage of cells that express PDX-1 in the nucleus (FIG. 8). These data show that Hes3 can be regulated not only directly by siRNA but also by other, indirect, stimuli. For example, by employing an inhibitor of Exendin-4 or its receptor nuclear Hes3 could be modulated.

REFERENCES

Altshuler E P, Serebryanaya D V, Katrukha A G. Generation of recombinant antibodies and means for increasing their affinity. 2010, Biochemistry (Mosc)., vol. 75(13), 1584
Androutsellis-Theotokis A, Leker R R, Soldner, F, Hoeppner D J, Ravin R, Poser S W, Rueger M A, Bae S K, Kittappa R and McKay R D. Notch signalling regulates stem cell numbers in vitro and in vivo. 2006, Nature, vol. 442(17), 823
Androutsellis-Theotokis A, Rueger M A, Park D M, Mkhikian H, Korb E, Poser S W, Walbridge S, Munasinghe J, Koretsky A P, Lonser R R and McKay R D. Targeting neural precursors in the adult brain rescues injured dopamine neurons. 2008, Cold Spring Harbor Laboratory Press, vol. LXXIII
Androutsellis-Theotokis A, Rueger M A, Park D M, Mkhikian H, Korb E, Poser S W, Walbridge S, Munasinghe J, Koretsky A P, Lonser R R, McKay R D, Targeting neural precursors in the adult brain rescues injured dopamine neurons. 2009, PNAS, vol. 106(32), 13570
Androutsellis-Theotokis A, Rueger M A, Park D M, Boyd J D, Padmanabhan R, Campanati L, Stewart C V, LeFranc Y, Plenz D, Walbridge S, Lonser R R, McKay R D. 2010a, PLoS One, vol. 5(2), e9414 Androutsellis-Theotokis A, Walbridge S, Park D M, Lonser R R, McKay R D. 2010b, PLoS One, vol. 5(5), e10841
Bakker A B, van den Oudenrijn S, Bakker A Q, Feller N, van Meijer M, Bia J A, Jongeneelen M A, Visser T J, Bijl N, Geuijen C A, Marissen W E, Radosevic K, Throsby M, Schuurhuis G J, Ossenkoppele G J, de Kruif J, Goudsmit J, Kruisbeek A M. C-type lectin-like molecule-1: a novel myeloid cell surface marker associated with acute myeloid leukemia 2004; Cancer Research, vol. 64(22), 8443
Bateman A, Coin L, Durbin R, Finn R D, Hollich V, Griffiths-Jones S, Khanna A, Marshall M, Moxon S, Sonnhammer E L, Studholme D J, Yeats C, Eddy S R. The Pfam protein families database. Nucleic Acids Res., 2004, vol. 32 (Database issue), 138.
Brunner T B, Kunz-Schughart, Grosse-Gehling P, Baumann M. Cancer Stem Cells as a Predictive Factor in Radiotherapy. Seminars in Radiation Oncology. 2012, vol. 22(2), 151
Black P., Brain Tumors, 1991, N Engl J Med. vol. 324, 1555
Carbone G M, McGuffie E M, Collier A, Catapano C V. Selective inhibition of transcription of the Ets2 gene in prostate cancer cells by a triplex-forming oligonucleotide, 2003, Nucleic Acids Res., vol. 31(3), 833
Chaffer C L, Weinberg R A. A perspective on cancer cell metastasis. 2011, Science. vol. 331(6024), 1559
Clayton S and Mousa S A, Therapeutics formulated to target cancer stem cells: Is it in our future?, 2011, Cancer Cell International, vol. 11(7)
Cole et al., Monoclonal antibodies and cancer therapy, 1985, Alan R. Liss, Inc, 77-96
Elbashir S M, Martinez J, Patkaniowska A, Lendeckel W, Tuschl T. Functional anatomy of siRNAs for mediating efficient RNAi in Drosophila melanogaster embryo lysate. 2001, EMBO J, vol. 20(23), 6877
Fattal E, Barratt G, Nanotechnologies and controlled release systems for the delivery of antisense oligonucleotides and small interfering RNA., 2009, Br J Pharmacol., vol. 157(2), 179
de Fougerolles A, Delivery vehicles for small interfering RNA in vivo., 2008, Hum Gene Ther., vol. 19(2), 125
Gavrilov K, Saltzman W M. Therapeutic siRNA: principles, challenges, and strategies. 2012, Yale J Biol Med., vol. 85(2), 187
Harlow E and Lane D, Antibodies, A Laboratory Manual, Cold Spring Harbor Laboratory Press, 1988
Harlow E and Lane D, Using Antibodies: A Laboratory Manual, Cold Spring Harbor Laboratory Press, 1999
Hatakeyama J, Bessho Y, Katoh K, Ookawara S, Fujioka M, Guillemot F, Kageyama R., Hes genes regulate size, shape and histogenesis of the nervous system by control of the timing of neural stem cell differentiation. 2004, Development. vol. 131(22), 5539
Hirata H., Tomita K., Bessho Y. and Kageyama R. Hes1 and Hes3 regulate maintenance of the isthmic organizer and development of the mid/hindbrain. 2001, EMBO J. vol. 20(16), 4454
Holliger P, Hudson P J. Engineered antibody fragments and the rise of single domains. 2005, Nat Biotechnol., vol. 23(9), 1126
Kalinina J, Peng J, Ritchie J C, Van Meir E G. Proteomics of gliomas: initial biomarker discovery and evolution of technology. 2011, Neuro Oncol., vol. 13(9), 926
Köhler G, Milstein C. Continuous cultures of fused cells secreting antibody of predefined specificity. Nature, 1975, vol. 256(5517), 495.
Kozbor D, 1983, Immunology Today, vol. 4, 7
Kubinyi, Hausch-Analysis and Related Approaches, VCH Verlag, Weinheim, 1992
Letunic I, Copley R R, Schmidt S, Ciccarelli F D, Doerks T, Schultz J, Ponting C P, Bork P. SMART 4.0: towards genomic data integration. Nucleic Acids Res., 2004, vol. 32 (Database issue), 142.
Li J, Sai T, Berger M, Chao Q, Davidson D, Deshmukh G, Drozdowski B, Ebel W, Harley S, Henry M, Jacob S, Kline B, Lazo E, Rotella F, Routhier E, Rudolph K, Sage J, Simon P, Yao J, Zhou Y, Kavuru M, Bonfield T, Thomassen M J, Sass P M, Nicolaides N C, Grasso L.

Human antibodies for immunotherapy development generated via a human B cell hybridoma technology., 2006, PNAS, vol. 103(10), 3557

Louis D N., Ohgaki H., Wiestler O D., Cavenee W K., Burger P C., Jouvet A., Scheithauer B W., Kleihues P. The 2007 WHO Classification of Tumours of the Central Nervous System, 2007, Acta Neuropathol., vol. 114(2), 97

Lu P Y, Woodle M C. Delivering small interfering RNA for novel therapeutics. 2008, Methods Mol Biol., vol. 437, 93

Magee J A., Piskounova E, Morrison S J. Cancer Stem Cells: Impact, Heterogeneity, and Uncertainty. 2012, Cancer Cell. Vol. 21(3), 283

Malmborg A C, Borrebaeck C A. BIAcore as a tool in antibody engineering. 1995, J Immunol Methods., vol. 183(1), 7

Melani C, Rivoltini L, Parmiani G, Calabretta B, Colombo M P. Inhibition of proliferation by c-myb antisense oligodeoxynucleotides in colon adenocarcinoma cell lines that express c-myb., 1991, vol. 51(11), 2897

Mulder N J, Apweiler R, Attwood T K, Bairoch A, Barrell D, Bateman A, Binns D, Biswas M, Bradley P, Bork P, Bucher P, Copley R R, Courcelle E, Das U, Durbin R, Falquet L, Fleischmann W, Griffiths-Jones S, Haft D, Harte N, Hulo N, Kahn D, Kanapin A, Krestyaninova M, Lopez R, Letunic I, Lonsdale D, Silventoinen V, Orchard S E, Pagni M, Peyruc D, Ponting C P, Selengut J D, Servant F, Sigrist C J, Vaughan R, Zdobnov E M. The InterPro Database, 2003 brings increased coverage and new features., 2003, Nucleic Acids Res., vol. 31(1), 315

Osborne S E, Matsumura I, Ellington A D. 1997, Curr Opin Chem Biol., vol. 1(1), 5

Park, D. M., Jung, J., Masjkur, J., Makrogkikas, S., Ebermann, D., Saha, S., Rogliano, R., Paolillo, N., Pacioni, S., McKay, R. D., Poser, S. & Androutsellis-Theotokis, A. (2013) Hes3 regulates cell number in cultures from glioblastoma multiforme with stem cell characteristics. Sci Rep, 3, 1095.

Paulo J A, Kadiyala V, Banks P A, Steen H, Conwell D L. Mass spectrometry-based proteomics for translational research: a technical overview. Yale J Biol Med. 2012 March; 85(1):59-73.

Petriz B A, Gomes C P, Rocha L A, Rezende T M, Franco O L. Proteomics applied to exercise physiology: a cutting-edge technology. Cell Physiol. 2012 March; 227(3):885-98.

Schier R, Marks J D. 1996, Hum Antibodies Hybridomas, vol. 7(3), 97

Schlatter D, Brack S, Banner D W, Batey S, Benz J, Bertschinger J, Huber W, Joseph C, Rufer A, van der Klooster A, Weber M, Grabulovski D, Hennig M. Generation, characterization and structural data of chymase binding proteins based on the human Fyn kinase SH3 domain. 2012, MAbs., vol. 4(4), 497

Shackleton M, Quintana E, Fearon E R, Morrison S J. Heterogeneity in Cancer: Cancer Stem Cells versus Clonal Evolution. 2009, Cell, vol. 138(5), 822

Singh S K, Hawkins C, Clarke I D, Squire J A, Bayani J, Hide T, Henkelman R M, Cusimano M D, Dirks P B. Identification of human brain tumour initiating cells. 2004, Nature, vol. 432(7015), 396

Stull R A, Szoka F C Jr. 1995, Pharm Res., vol. 12(4), 465

Tuschl T, RNA interference and small interfering RNAs, Chembiochem., 2001, vol 2(4), 239

Venere M., Fine H A., Dirks P B., Rich J N., Cancer stem cells in gliomas: Identifying and understanding the apex cell in cancer's hierarchy. 2011, Glia, Special Issue: Glioma, vol. 59(8), 1148

Zamore P D, RNA interference: listening to the sound of silence. Nat. Struct. Biol., 2001, vol 8(9), 746

The invention claimed is:

1. A method for treating a subject having a brain tumour, the method comprising:
    determining the amount of Hes3 protein in a cerebrospinal fluid (CSF) sample obtained from the subject; and
    administering to the subject an inhibitor of Hairy and Enhancer of Split 3 (Hes3) in a therapeutically effective amount to reduce the tumour burden or eradicate the tumour in the subject;
    wherein the inhibitor comprises an anti-Hes3 siRNA.

2. The method according to claim 1, wherein the amount of Hes3 is determined using an antibody and/or mass spectrometry.

3. The method according to claim 1, wherein the amount of Hes3 protein positively correlates with the aggressiveness of the tumour.

4. The method according to claim 1, wherein the subject is a human.

5. The method according to claim 1, wherein the inhibitor reduces the number of or eliminates cancer stem cells (CSCs).

6. The method according to claim 1, wherein the brain tumour comprises a glioma, a glioblastoma, a meningioma, a pituitary adenoma, a vestibular schwannoma, a primary CNS lymphoma, or a medulloblastoma.

7. The method according to claim 1, wherein the inhibitor is administered in combination with a second therapeutic compound and/or radiation.

8. The method according to claim 7, wherein the second compound is a chemotherapeutic compound.

9. The method of claim 1, wherein the brain tumor comprises a primary brain tumor.

10. The method of claim 1, wherein the brain tumor comprises a meningioma I.

11. The method of claim 1, wherein the brain tumor comprises a glioblastoma multiforme grade IV.

12. The method according to claim 1, wherein the anti-Hes3 siRNA is selected from the group consisting of sc88003, SR318208A, and SR318208C.

13. The method of claim 1, wherein the Hes3 protein in the CSF sample comprises an increase of at least 1.5 fold the normal value.

* * * * *